United States Patent [19]

Shima et al.

[11] Patent Number: 5,328,836
[45] Date of Patent: Jul. 12, 1994

[54] PLASMIDS CONTAINING DNA ENCODING THE AMINO ACID SEQUENCE OF TCF-II AND USE THEREOF

[75] Inventors: Nobuyuki Shima, Oyama; Kanji Higashio, Kawagoe; Masaya Nagao, Kyoto; Fumiko Oogaki, Utsunomiya; Hiroaki Takaoka; Eisuke Tsuda, both of Shimotsuga, all of Japan

[73] Assignee: Snow Brand Milk Products Co., Ltd., Sapporo, Japan

[21] Appl. No.: 838,410

[22] PCT Filed: Jul. 15, 1991

[86] PCT No.: PCT/JP91/00942

§ 371 Date: Mar. 11, 1992

§ 102(e) Date: Mar. 11, 1992

[87] PCT Pub. No.: WO92/01053

PCT Pub. Date: Jan. 23, 1992

[30] Foreign Application Priority Data

Jul. 13, 1990 [JP] Japan .................................. 2-185852

[51] Int. Cl.$^5$ .............................................. C12P 21/02
[52] U.S. Cl. ................................ 435/69.4; 435/240.1; 435/320.1; 536/23.51; 935/13; 935/70

[58] Field of Search ..................... 536/23.51; 435/69.4, 435/240.1; 514/2

[56] References Cited

PUBLICATIONS

Biochem Biophys Res Comm 172(1): 321–327 Oct. 5, 1990 T. Seki et al. "Isolation & Expression . . . ".
S. Sone et al. Biotherapy 1: 233–243 1989, "Effector Mechamism . . . ".
Miyazawa et al., "Molecular Cloning and Sequence Analysis of cDNA for Human Hepatocyte Growth Factor," Biochemical Biophysical Research Communications, 170, pp. 967–973 (1989).

Primary Examiner—Robert J. Hill, Jr.
Assistant Examiner—L. Spector
Attorney, Agent, or Firm—Millen, White, Zelano & Branigan

[57] ABSTRACT

Plasmids containing DNA encoding the amino acid sequence of a novel glycoprotein (TCF-II) derived from human fibroblasts, transformed cells with the plasmids and production method of rTCF-II using the transformed cells. rTCF-II can be used as a hepatocyte growth factor or a tumor cytotoxic factor.

5 Claims, 13 Drawing Sheets

```
                    -110       -100       -90       -80       -70       -60
                                                          TAGGCACTGACTCCGAA
         -50       -40       -30       -20       -10         0
CAGGATTCTTTCACCCAGGCATCTCCTCCAGAGGGATCCGCCAGCCCGTCCAGCAGCACC
          10        20        30        40        50        60
ATGTGGGTGACCAAACTCCTGCCAGCCCTGCTGCTGCAGCATGTCCTCCTGCATCTCCTC
 M  W  V  T  K  L  L  P  A  L  L  L  Q  H  V  L  L  H  L  L
          70        80        90       100       110       120
CTGCTCCCCATCGCCATCCCCTATGCAGAGGGACAAAGGAAAAGAAGAAATACAATTCAT
 L  L  P  I  A  I  P  Y  A  E  G  Q  R  K  R  R  N  T  I  H
         130       140       150       160       170       180
GAATTCAAAAAATCAGCAAAGACTACCCTAATCAAAATAGATCCAGCACTGAAGATAAAA
 E  F  K  K  S  A  K  T  T  L  I  K  I  D  P  A  L  K  I  K
         190       200       210       220       230       240
ACCAAAAAAGTGAATACTGCAGACCAATGTGCTAATAGATGTACTAGGAATAAAGGACTT
 T  K  K  V  N  T  A  D  Q  C  A  N  R  C  T  R  N  K  G  L
         250       260       270       280       290       300
CCATTCACTTGCAAGGCTTTTGTTTTTGATAAAGCAAGAAAACAATGCCTCTGGTTCCCC
 P  F  T  C  K  A  F  V  F  D  K  A  R  K  Q  C  L  W  F  P
         310       320       330       340       350       360
TTCAATAGCATGTCAAGTGGAGTGAAAAAAGAATTTGGCCATGAATTTGACCTCTATGAA
 F  N  S  M  S  S  G  V  K  K  E  F  G  H  E  F  D  L  Y  E
         370       380       390       400       410       420
AACAAAGACTACATTAGAAACTGCATCATTGGTAAAGGACGCAGCTACAAGGGAACAGTA
 N  K  D  Y  I  R  N  C  I  I  G  K  R  S  Y  K  G  T  V
         430       440       450       460       470       480
TCTATCACTAAGAGTGGCATCAAATGTCAGCCCTGGAGTTCCATGATACCACACGAACAC
 S  I  T  K  S  G  I  K  C  Q  P  W  S  S  M  I  P  H  E  H
         490       500       510       520       530       540
AGCTATCGGGGTAAAGACCTACAGGAAAACTACTGTCGAAATCCTCGAGGGGAAGAAGGG
 S  Y  R  G  K  D  L  Q  E  N  Y  C  R  N  P  R  G  E  E  G
         550       560       570       580       590       600
GGACCCTGGTGTTTCACAAGCAATCCAGAGGTACGCTACGAAGTCTGTGACATTCCTCAG
 G  P  W  C  F  T  S  N  P  E  V  R  Y  E  V  C  D  I  P  Q
         610'      620       630       640       650       660
TGTTCAGAAGTTGAATGCATGACCTGCAATGGGGAGAGTTATCGAGGTCTCATGGATCAT
 C  S  E  V  E  C  M  T  C  N  G  E  S  Y  R  G  L  M  D  H
```

```
         670       680       690       700       710       720
ACAGAATCAGGCAAGATTTGTCAGCGCTGGGATCATCAGACACCACACCGGCACAAATTC
 T  E  S  G  K  I  C  Q  R  W  D  H  Q  T  P  H  R  H  K  F
         730       740       750       760       770       780
TTGCCTGAAAGATATCCCGACAAGGGCTTTGATGATAATTATTGCCGCAATCCCGATGGC
 L  P  E  R  Y  P  D  K  G  F  D  D  N  Y  C  R  N  P  D  G
         790       800       810       820       830       840
CAGCCGAGGCCATGGTGCTATACTCTTGACCCTCACACCCGCTGGGAGTACTGTGCAATT
 Q  P  R  P  W  C  Y  T  L  D  P  H  T  R  W  E  Y  C  A  I
         850       860       870       880       890       900
AAAACATGCGCTGACAATACTATGAATGACACTGATGTTCCTTTGGAAACAACTGAATGC
 K  T  C  A  D  N  T  M  N  D  T  D  V  P  L  E  T  T  E  C
         910       920       930       940       950       960
ATCCAAGGTCAAGGAGAAGGCTACAGGGGCACTGTCAATACCATTTGGAATGGAATTCCA
 I  Q  G  Q  G  E  G  Y  R  G  T  V  N  T  I  W  N  G  I  P
         970       980       990      1000      1010      1020
TGTCAGCGTTGGGATTCTCAGTATCCTCACGAGCATGACATGACTCCTGAAAATTTCAAG
 C  Q  R  W  D  S  Q  Y  P  H  E  H  D  M  T  P  E  N  F  K
        1030      1040      1050      1060      1070      1080
TGCAAGGACCTACGAGAAAATTACTGCCGAAATCCAGATGGGTCTGAATCACCCTGGTGT
 C  K  D  L  R  E  N  Y  C  R  N  P  D  G  S  E  S  P  W  C
        1090      1100      1110      1120      1130      1140
TTTACCACTGATCCAAACATCCGAGTTGGCTACTGCTCCCAAATTCCAAACTGTGATATG
 F  T  T  D  P  N  I  R  V  G  Y  C  S  Q  I  P  N  C  D  M
        1150      1160      1170      1180      1190      1200
TCACATGGACAAGATTGTTATCGTGGGAATGGCAAAAATTATATGGGCAACTTATCCCAA
 S  H  G  Q  D  C  Y  R  G  N  G  K  N  Y  M  G  N  L  S  Q
                        Internal amino acid sequence in α-chain
        1210      1220      1230      1240      1250      1260
ACAAGATCTGGACTAACATGTTCAATGTGGGACAAGAACATGGAAGACTTACATCGTCAT
 T  R  S  G  L  T  C  S  M  W  D  K  N  M  E  D  L  H  R  H
        1270      1280      1290      1300      1310      1320
ATCTTCTGGGAACCAGATGCAAGTAAGCTGAATGAGAATTACTGCCGAAATCCAGATGAT
 I  F  W  E  P  D  A  S  K  L  N  E  N  Y  C  R  N  P  D  D
        1330      1340      1350      1360      1370      1380
GATGCTCATGGACCCTGGTGCTACACGGGAAATCCACTCATTCCTTGGGATTATTGCCCT
 D  A  H  G  P  W  C  Y  T  G  N  P  L  I  P  W  D  Y  C  P
        1390      1400      1410      1420      1430      1440
ATTTCTCGTTGTGAAGGTGATACCACACCTACAATAGTCAATTTAGACCATCCGTAATA
 I  S  R  C  E  G  D  T  T  P  T  I  V  N  L  D  H  P  V  I
```

```
                              -110        -100        -90         -80         -70          -60
                                                                              TAGGCACTGACTCCGAA
       -50         -40         -30         -20         -10            0
CAGGATTCTTTCACCCAGGCATCTCCTCCAGAGGGATCCGCCAGCCCGTCCAGCAGCACC
         10          20          30          40          50          60
ATGTGGGTGACCAAACTCCTGCCAGCCCTGCTGCTGCAGCATGTCCTCCTGCATCTCCTC
 M  W  V  T  K  L  L  P  A  L  L  L  Q  H  V  L  L  H  L  L
         70          80          90         100         110         120
CTGCTCCCCATCGCCATCCCCTATGCAGAGGGACAAAGGAAAAGAAGAAATACAATTCAT
 L  L  P  I  A  I  P  Y  A  E  G  Q  R  K  R  R  N  T  I  H
        130         140         150         160         170         180
GAATTCAAAAAATCAGCAAAGACTACCCTAATCAAAATAGATCCAGCACTGAAGATAAAA
 E  F  K  K  S  A  K  T  T  L  I  K  I  D  P  A  L  K  I  K
        190         200         210         220         230         240
ACCAAAAAAGTGAATACTGCAGACCAATGTGCTAATAGATGTACTAGGAATAAAGGACTT
 T  K  K  V  N  T  A  D  Q  C  A  N  R  C  T  R  N  K  G  L
        250         260         270         280         290         300
CCATTCACTTGCAAGGCTTTTGTTTTTGATAAAGCAAGAAAACAATGCCTCTGGTTCCCC
 P  F  T  C  K  A  F  V  F  D  K  A  R  K  Q  C  L  W  F  P
        310         320         330         340         350         360
TTCAATAGCATGTCAAGTGGAGTGAAAAAAGAATTTGGCCATGAATTTGACCTCTATGAA
 F  N  S  M  S  S  G  V  K  K  E  F  G  H  E  F  D  L  Y  E
        370         380         390         400         410         420
AACAAAGACTACATTAGAAACTGCATCATTGGTAAAGGACGCAGCTACAAGGGAACAGTA
 N  K  D  Y  I  R  N  C  I  I  G  K  G  R  S  Y  K  G  T  V
        430         440         450         460         470         480
TCTATCACTAAGAGTGGCATCAAATGTCAGCCCTGGAGTTCCATGATACCACACGAACAC
 S  I  T  K  S  G  I  K  C  Q  P  W  S  S  M  I  P  H  E  H
        490         500         510         520         530         540
AGCTATCGGGGTAAAGACCTACAGGAAAACTACTGTCGAAATCCTCGAGGGGAAGAAGGG
 S  Y  R  G  K  D  L  Q  E  N  Y  C  R  N  P  R  G  E  E  G
        550         560         570         580         590         600
GGACCCTGGTGTTTCACAAGCAATCCAGAGGTACGCTACGAAGTCTGTGACATTCCTCAG
 G  P  W  C  F  T  S  N  P  E  V  R  Y  E  V  C  D  I  P  Q
        610         620         630         640         650         660
TGTTCAGAAGTTGAATGCATGACCTGCAATGGGGAGAGTTATCGAGGTCTCATGGATCAT
 C  S  E  V  E  C  M  T  C  N  G  E  S  Y  R  G  L  M  D  H
```

FIG. IA

```
              670       680       690       700       710       720
ACAGAATCAGGCAAGATTTGTCAGCGCTGGGATCATCAGACACCACACCGGCACAAATTC
 T  E  S  G  K  I  C  Q  R  W  D  H  Q  T  P  H  R  H  K  F 730       740       750       760       770       780
TTGCCTGAAAGATATCCCGACAAGGGCTTTGATGATAATTATTGCCGCAATCCCGATGGC
 L  P  E  R  Y  P  D  K  G  F  D  D  N  Y  C  R  N  P  D  G 790       800       810       820       830       840
CAGCCGAGGCCATGGTGCTATACTCTTGACCCTCACACCCGCTGGGAGTACTGTGCAATT
 Q  P  R  P  W  C  Y  T  L  D  P  H  T  R  W  E  Y  C  A  I 850       860       870       880       890       900
AAAACATGCGCTGACAATACTATGAATGACACTGATGTTCCTTTGGAAACAACTGAATGC
 K  T  C  A  D  N  T  M  N  D  T  D  V  P  L  E  T  T  E  C 910       920       930       940       950       960
ATCCAAGGTCAAGGAGAAGGCTACAGGGGCACTGTCAATACCATTTGGAATGGAATTCCA
 I  Q  G  Q  G  E  G  Y  R  G  T  V  N  T  I  W  N  G  I  P 970       980       990      1000      1010      1020
TGTCAGCGTTGGGATTCTCAGTATCCTCACGAGCATGACATGACTCCTGAAAATTTCAAG
 C  Q  R  W  D  S  Q  Y  P  H  E  H  D  M  T  P  E  N  F  K 1030      1040      1050      1060      1070      1080
TGCAAGGACCTACGAGAAAATTACTGCCGAAATCCAGATGGGTCTGAATCACCCTGGTGT
 C  K  D  L  R  E  N  Y  C  R  N  P  D  G  S  E  S  P  W  C 1090      1100      1110      1120      1130      1140
TTTACCACTGATCCAAACATCCGAGTTGGCTACTGCTCCCAAATTCCAAACTGTGATATG
 F  T  T  D  P  N  I  R  V  G  Y  C  S  Q  I  P  N  C  D  M 1150      1160      1170      1180      1190      1200
TCACATGGACAAGATTGTTATCGTGGGAATGGCAAAAATTATATGGGCAACTTATCCCAA
 S  H  G  Q  D  C  Y  R  G  N  G  K  N  Y  M  G  N  L  S  Q
                                    Internal amino acid sequence in α-chain
             1210      1220      1230      1240      1250      1260
ACAAGATCTGGACTAACATGTTCAATGTGGGACAAGAACATGGAAGACTTACATCGTCAT
 T  R  S  G  L  T  C  S  M  W  D  K  N  M  E  D  L  H  R  H 1270      1280      1290      1300      1310      1320
ATCTTCTGGGAACCAGATGCAAGTAAGCTGAATGAGAATTACTGCCGAAATCCAGATGAT
 I  F  W  E  P  D  A  S  K  L  N  E  N  Y  C  R  N  P  D  D 1330      1340      1350      1360      1370      1380
GATGCTCATGGACCCTGGTGCTACACGGGAAATCCACTCATTCCTTGGGATTATTGCCCT
 D  A  H  G  P  W  C  Y  T  G  N  P  L  I  P  W  D  Y  C  P 1390      1400      1410      1420      1430      1440
ATTTCTCGTTGTGAAGGTGATACCACACCTACAATAGTCAATTTAGACCATCCCGTAATA
 I  S  R  C  E  G  D  T  T  P  T  I  V  N  L  D  H  P  V  I
```

FIG. IB

```
      1450      1460      1470      1480      1490      1500
TCTTGTGCCAAAACGAAACAATTGCGAGTTGTAAATGGGATTCCAACACGAACAAACATA
 S  C  A  K  T  K  Q  L  R  V  V  N  G  I  P  T  R  T  N  I
                            ↑
                         N-terminus of β-chain
                         N-terminal amino acid sequence of β-chain
      1510      1520      1530      1540      1550      1560
GGATGGATGGTTAGTTTGAGATACAGAAATAAACATATCTGCGGAGGATCATTGATAAAG
 G  W  M  V  S  L  R  Y  R  N  K  H  I  C  G  G  S  L  I  K 1570      1580      1590      1600      1610      1620
GAGAGTTGGGTTCTTACTGCACGACAGTGTTTCCCTTCTCGAGACTTGAAAGATTATGAA
 E  S  W  V  L  T  A  R  Q  C  F  P  S  R  D  L  K  D  Y  E 1630      1640      1650      1660      1670      1680
GCTTGGCTTGGAATTCATGATGTCCACGGAAGAGGAGATGAGAAATGCAAACAGGTTCTC
 A  W  L  G  I  H  D  V  H  G  R  G  D  E  K  C  K  Q  V  L 1690      1700      1710      1720      1730      1740
AATGTTTCCCAGCTGGTATATGGCCCTGAAGGATCAGATCTGGTTTTAATGAAGCTTGCC
 N  V  S  Q  L  V  Y  G  P  E  G  S  D  L  Y  L  M  K  L  A 1750      1760      1770      1780      1790      1800
AGGCCTGCTGTCCTGGATGATTTTGTTAGTACGATTGATTTACCTAATTATGGATGCACA
 R  P  A  V  L  D  D  F  V  S  T  I  D  L  P  N  Y  G  C  T 1810      1820      1830      1840      1850      1860
ATTCCTGAAAAGACCAGTTGCAGTGTTTATGGCTGGGGCTACACTGGATTGATCAACTAT
 I  P  E  K  T  S  C  S  V  Y  G  W  G  Y  T  G  L  I  N  Y
                                  Internal amino acid sequence in β-chain
      1870      1880      1890      1900      1910      1920
GATGGCCTATTACGAGTGGCACATCTCTATATAATGGGAAATGAGAAATGCAGCCAGCAT
 D  G  L  L  R  V  A  H  L  Y  I  M  G  N  E  K  C  S  Q  H 1930      1940      1950      1960      1970      1980
CATCGAGGGAAGGTGACTCTGAATGAGTCTGAAATATGTGCTGGGGCTGAAAAGATTGGA
 H  R  G  K  V  T  L  N  E  S  E  I  C  A  G  A  E  K  I  G 1990      2000      2010      2020      2030      2040
TCAGGACCATGTGAGGGGGATTATGGTGGCCCACTTGTTTGTGAGCAACATAAAATGAGA
 S  G  P  C  E  G  D  Y  G  G  P  L  V  C  E  Q  H  K  M  R 2050      2060      2070      2080      2090      2100
ATGGTTCTTGGTGTCATTGTTCCTGGTCGTGGATGTGCCATTCCAAATCGTCCTGGTATT
 M  V  L  G  V  I  V  P  G  R  G  C  A  I  P  N  R  P  G  I 2110      2120      2130      2140      2150      2160
TTTGTCCGAGTAGCATATTATGCAAAATGGATACACAAAATTATTTTAACATATAAGGTA
 F  V  R  V  A  Y  Y  A  K  W  I  H  K  I  I  L  T  Y  K  V 2170      2180      2190      2200      2210
CCACAGTCATAGCTGAAGTAAGTGTGTCTGAAGCACCCACCAATACAACTGT
 P  Q  S  *
```

FIG. IC

SEQUENCE LISTING (1) GENERAL INFORMATION:

(i i i) NUMBER OF SEQUENCES: 11

(2) INFORMATION FOR SEQ ID NO:1:

(i) SEQUENCE CHARACTERISTICS:
      (A) LENGTH: 723 amino acids
      (B) TYPE: amino acid
      (C) STRANDEDNESS: single
      (D) TOPOLOGY: linear (i i) MOLECULE TYPE: protein (v i) ORIGINAL SOURCE:
      (A) ORGANISM: Homo sapiens
      (G) CELL TYPE: Fibroblast (i x) FEATURE:
      (A) NAME/KEY: Domain
      (B) LOCATION: 393..405
      (D) OTHER INFORMATION: /note="INTERNAL AMINO ACID SEQUENCE IN ALPHA-CHAIN"

(i x) FEATURE:
      (A) NAME/KEY: Protein
      (B) LOCATION: 490..505
      (D) OTHER INFORMATION: /note="N-TERMINAL AMINO ACID SEQUENCE OF BETA-CHAIN"

(i x) FEATURE:
      (A) NAME/KEY: Domain
      (B) LOCATION: 605..623
      (D) OTHER INFORMATION: /note="INTERNAL AMINO ACID SEQUENCE IN BETA-CHAIN"

(x i) SEQUENCE DESCRIPTION: SEQ ID NO:1:

```
Met Trp Val Thr Lys Leu Leu Pro Ala Leu Leu Leu Gln His Val Leu
                -485            -480                    -475

Leu His Leu Leu Leu Leu Pro Ile Ala Ile Pro Tyr Ala Glu Gly Gln
                -470            -465                -460

Arg Lys Arg Arg Asn Thr Ile His Glu Phe Lys Lys Ser Ala Lys Thr
            -455            -450                -445

Thr Leu Ile Lys Ile Asp Pro Ala Leu Lys Ile Lys Thr Lys Lys Val
    -440            -435                -430

Asn Thr Ala Asp Gln Cys Ala Asn Arg Cys Thr Arg Asn Lys Gly Leu
-425                -420                -415            -410

Pro Phe Thr Cys Lys Ala Phe Val Phe Asp Lys Ala Arg Lys Gln Cys
                -405            -400                    -395

Leu Trp Phe Pro Phe Asn Ser Met Ser Ser Gly Val Lys Lys Glu Phe
                -390            -385                -380

Gly His Glu Phe Asp Leu Tyr Glu Asn Lys Asp Tyr Ile Arg Asn Cys
            -375            -370                -365

Ile Ile Gly Lys Gly Arg Ser Tyr Lys Gly Thr Val Ser Ile Thr Lys
    -360            -355                -350

Ser Gly Ile Lys Cys Gln Pro Trp Ser Ser Met Ile Pro His Glu His
-345                -340                -335                -330

Ser Tyr Arg Gly Lys Asp Leu Gln Glu Asn Tyr Cys Arg Asn Pro Arg
                    -325                -320                -315
```

-continued

```
Gly Glu Glu Gly Gly Pro Trp Cys Phe Thr Ser Asn Pro Glu Val Arg
        -310            -305                -300
Tyr Glu Val Cys Asp Ile Pro Gln Cys Ser Glu Val Glu Cys Met Thr
    -295                -290                -285
Cys Asn Gly Glu Ser Tyr Arg Gly Leu Met Asp His Thr Glu Ser Gly
    -280                -275                -270
Lys Ile Cys Gln Arg Trp Asp His Gln Thr Pro His Arg His Lys Phe
-265            -260                -255                    -250
Leu Pro Glu Arg Tyr Pro Asp Lys Gly Phe Asp Asp Asn Tyr Cys Arg
                -245                -240                -235
Asn Pro Asp Gly Gln Pro Arg Pro Trp Cys Tyr Thr Leu Asp Pro His
            -230                -225                -220
Thr Arg Trp Glu Tyr Cys Ala Ile Lys Thr Cys Ala Asp Asn Thr Met
        -215            -210            -205
Asn Asp Thr Asp Val Pro Leu Glu Thr Thr Glu Cys Ile Gln Gly Gln
            -200            -195            -190
Gly Glu Gly Tyr Arg Gly Thr Val Asn Thr Ile Trp Asn Gly Ile Pro
-185                -180                -175                -170
Cys Gln Arg Trp Asp Ser Gln Tyr Pro His Glu His Asp Met Thr Pro
            -165                -160                -155
Glu Asn Phe Lys Cys Lys Asp Leu Arg Glu Asn Tyr Cys Arg Asn Pro
            -150            -145                -140
Asp Gly Ser Glu Ser Pro Trp Cys Phe Thr Thr Asp Pro Asn Ile Arg
        -135                -130                -125
Val Gly Tyr Cys Ser Gln Ile Pro Asn Cys Asp Met Ser His Gly Gln
    -120            -115                -110
Asp Cys Tyr Arg Gly Asn Gly Lys Asn Tyr Met Gly Asn Leu Ser Gln
-105            -100                -95                     -90
Thr Arg Ser Gly Leu Thr Cys Ser Met Trp Asp Lys Asn Met Glu Asp
            -85                 -80                     -75
Leu His Arg His Ile Phe Trp Glu Pro Asp Ala Ser Lys Leu Asn Glu
        -70                 -65                 -60
Asn Tyr Cys Arg Asn Pro Asp Asp Asp Ala His Gly Pro Trp Cys Tyr
    -55                 -50                 -45
Thr Gly Asn Pro Leu Ile Pro Trp Asp Tyr Cys Pro Ile Ser Arg Cys
    -40                 -35                 -30
Glu Gly Asp Thr Thr Pro Thr Ile Val Asn Leu Asp His Pro Val Ile
-25                 -20                 -15                 -10
Ser Cys Ala Lys Thr Lys Gln Leu Arg Val Val Asn Gly Ile Pro Thr
            -5                  1                   5
Arg Thr Asn Ile Gly Trp Met Val Ser Leu Arg Tyr Arg Asn Lys His
        10                  15                  20
Ile Cys Gly Gly Ser Leu Ile Lys Glu Ser Trp Val Leu Thr Ala Arg
    25                  30                  35
Gln Cys Phe Pro Ser Arg Asp Leu Lys Asp Tyr Glu Ala Trp Leu Gly
40                  45                  50                  55
Ile His Asp Val His Gly Arg Gly Asp Glu Lys Cys Lys Gln Val Leu
                60                  65                  70
Asn Val Ser Gln Leu Val Tyr Gly Pro Glu Gly Ser Asp Leu Val Leu
            75                  80                  85
Met Lys Leu Ala Arg Pro Ala Val Leu Asp Asp Phe Val Ser Thr Ile
        90                  95                  100
Asp Leu Pro Asn Tyr Gly Cys Thr Ile Pro Glu Lys Thr Ser Cys Ser
        105                 110                 115
```

| | | | | | | | | | | | | | | |
|---|---|---|---|---|---|---|---|---|---|---|---|---|---|---|
| Val | Tyr | Gly | Trp | Gly | Tyr | Thr | Gly | Leu | Ile | Asn | Tyr | Asp | Gly | Leu | Leu |
| 120 | | | | | 125 | | | | | 130 | | | | | 135 |

| Arg | Val | Ala | His | Leu | Tyr | Ile | Met | Gly | Asn | Glu | Lys | Cys | Ser | Gln | His |
|---|---|---|---|---|---|---|---|---|---|---|---|---|---|---|---|
| | | | | 140 | | | | | 145 | | | | | 150 | |

| His | Arg | Gly | Lys | Val | Thr | Leu | Asn | Glu | Ser | Glu | Ile | Cys | Ala | Gly | Ala |
|---|---|---|---|---|---|---|---|---|---|---|---|---|---|---|---|
| | | | | 155 | | | | | 160 | | | | | 165 | |

| Glu | Lys | Ile | Gly | Ser | Gly | Pro | Cys | Glu | Gly | Asp | Tyr | Gly | Gly | Pro | Leu |
|---|---|---|---|---|---|---|---|---|---|---|---|---|---|---|---|
| | | | 170 | | | | | 175 | | | | | 180 | | |

| Val | Cys | Glu | Gln | His | Lys | Met | Arg | Met | Val | Leu | Gly | Val | Ile | Val | Pro |
|---|---|---|---|---|---|---|---|---|---|---|---|---|---|---|---|
| | 185 | | | | | 190 | | | | | 195 | | | | |

| Gly | Arg | Gly | Cys | Ala | Ile | Pro | Asn | Arg | Pro | Gly | Ile | Phe | Val | Arg | Val |
|---|---|---|---|---|---|---|---|---|---|---|---|---|---|---|---|
| 200 | | | | | 205 | | | | | 210 | | | | | 215 |

| Ala | Tyr | Tyr | Ala | Lys | Trp | Ile | His | Lys | Ile | Ile | Leu | Thr | Tyr | Lys | Val |
|---|---|---|---|---|---|---|---|---|---|---|---|---|---|---|---|
| | | | | 220 | | | | | 225 | | | | | 230 | |

| Pro | Gln | Ser |
|---|---|---|

(2) INFORMATION FOR SEQ ID NO:2:

(i) SEQUENCE CHARACTERISTICS:
        (A) LENGTH: 2289 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens
        (G) CELL TYPE: Fibroblast (xi) SEQUENCE DESCRIPTION: SEQ ID NO:2:

| | | | | | |
|---|---|---|---|---|---|
| TAGGCACTGA | CTCCGAACAG | GATTCTTTCA | CCCAGGCATC | TCCTCCAGAG | GGATCCGCCA | 60 |
| GCCCGTCCAG | CAGCACCATG | TGGGTGACCA | AACTCCTGCC | AGCCCTGCTG | CTGCAGCATG | 120 |
| TCCTCCTGCA | TCTCCTCCTG | CTCCCCATCG | CCATCCCCTA | TGCAGAGGGA | CAAAGGAAAA | 180 |
| GAAGAAATAC | AATTCATGAA | TTCAAAAAAT | CAGCAAAGAC | TACCCTAATC | AAAATAGATC | 240 |
| CAGCACTGAA | GATAAAAACC | AAAAAAGTGA | ATACTGCAGA | CCAATGTGCT | AATAGATGTA | 300 |
| CTAGGAATAA | AGGACTTCCA | TTCACTTGCA | AGGCTTTTGT | TTTTGATAAA | GCAAGAAAAC | 360 |
| AATGCCTCTG | GTTCCCCTTC | AATAGCATGT | CAAGTGGAGT | GAAAAAAGAA | TTTGGCCATG | 420 |
| AATTTGACCT | CTATGAAAAC | AAAGACTACA | TTAGAAACTG | CATCATTGGT | AAAGGACGCA | 480 |
| GCTACAAGGG | AACAGTATCT | ATCACTAAGA | GTGGCATCAA | ATGTCAGCCC | TGGAGTTCCA | 540 |
| TGATACCACA | CGAACACAGC | TATCGGGGTA | AAGACCTACA | GGAAAACTAC | TGTCGAAATC | 600 |
| CTCGAGGGGA | AGAAGGGGGA | CCCTGGTGTT | TCACAAGCAA | TCCAGAGGTA | CGCTACGAAG | 660 |
| TCTGTGACAT | TCCTCAGTGT | TCAGAAGTTG | AATGCATGAC | CTGCAATGGG | GAGAGTTATC | 720 |
| GAGGTCTCAT | GGATCATACA | GAATCAGGCA | AGATTTGTCA | GCGCTGGGAT | CATCAGACAC | 780 |
| CACACCGGCA | CAAATTCTTG | CCTGAAAGAT | ATCCCGACAA | GGGCTTTGAT | GATAATTATT | 840 |
| GCCGCAATCC | CGATGGCCAG | CCGAGGCCAT | GGTGCTATAC | TCTTGACCCT | CACACCCGCT | 900 |
| GGGAGTACTG | TGCAATTAAA | ACATGCGCTG | ACAATACTAT | GAATGACACT | GATGTTCCTT | 960 |
| TGGAAACAAC | TGAATGCATC | CAAGGTCAAG | GAGAAGGCTA | CAGGGGCACT | GTCAATACCA | 1020 |
| TTTGGAATGG | AATTCCATGT | CAGCGTTGGG | ATTCTCAGTA | TCCTCACGAG | CATGACATGA | 1080 |
| CTCCTGAAAA | TTTCAAGTGC | AAGGACCTAC | GAGAAAATTA | CTGCCGAAAT | CCAGATGGGT | 1140 |
| CTGAATCACC | CTGGTGTTTT | ACCACTGATC | CAAACATCCG | AGTTGGCTAC | TGCTCCCAAA | 1200 |
| TTCCAAACTG | TGATATGTCA | CATGGACAAG | ATTGTTATCG | TGGGAATGGC | AAAAATTATA | 1260 |

| | | | | | |
|---|---|---|---|---|---|
| TGGGCAACTT | ATCCCAAACA | AGATCTGGAC | TAACATGTTC | AATGTGGGAC | AAGAACATGG 1320 |
| AAGACTTACA | TCGTCATATC | TTCTGGGAAC | CAGATGCAAG | TAAGCTGAAT | GAGAATTACT 1380 |
| GCCGAAATCC | AGATGATGAT | GCTCATGGAC | CCTGGTGCTA | CACGGGAAAT | CCACTCATTC 1440 |
| CTTGGGATTA | TTGCCCTATT | TCTCGTTGTG | AAGGTGATAC | CACACCTACA | ATAGTCAATT 1500 |
| TAGACCATCC | CGTAATATCT | TGTGCCAAAA | CGAAACAATT | GCGAGTTGTA | AATGGGATTC 1560 |
| CAACACGAAC | AAACATAGGA | TGGATGGTTA | GTTTGAGATA | CAGAAATAAA | CATATCTGCG 1620 |
| GAGGATCATT | GATAAGGAG | AGTTGGGTTC | TTACTGCACG | ACAGTGTTTC | CCTTCTCGAG 1680 |
| ACTTGAAAGA | TTATGAAGCT | TGGCTTGGAA | TTCATGATGT | CCACGGAAGA | GGAGATGAGA 1740 |
| AATGCAAACA | GGTTCTCAAT | GTTTCCCAGC | TGGTATATGG | CCCTGAAGGA | TCAGATCTGG 1800 |
| TTTTAATGAA | GCTTGCCAGG | CCTGCTGTCC | TGGATGATTT | TGTTAGTACG | ATTGATTTAC 1860 |
| CTAATTATGG | ATGCACAATT | CCTGAAAAGA | CCAGTTGCAG | TGTTTATGGC | TGGGGCTACA 1920 |
| CTGGATTGAT | CAACTATGAT | GGCCTATTAC | GAGTGGCACA | TCTCTATATA | ATGGGAAATG 1980 |
| AGAAATGCAG | CCAGCATCAT | CGAGGGAAGG | TGACTCTGAA | TGAGTCTGAA | ATATGTGCTG 2040 |
| GGGCTGAAAA | GATTGGATCA | GGACCATGTG | AGGGGGATTA | TGGTGGCCCA | CTTGTTTGTG 2100 |
| AGCAACATAA | AATGAGAATG | GTTCTTGGTG | TCATTGTTCC | TGGTCGTGGA | TGTGCCATTC 2160 |
| CAAATCGTCC | TGGTATTTTT | GTCCGAGTAG | CATATTATGC | AAAATGGATA | CACAAAATTA 2220 |
| TTTTAACATA | TAAGGTACCA | CAGTCATAGC | TGAAGTAAGT | GTGTCTGAAG | CACCCACCAA 2280 |
| TACAACTGT | | | | | 2289 |

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:3:

Val  Val  Asn  Gly  Ile  Pro  Thr
  1                  5

( 2 ) INFORMATION FOR SEQ ID NO:4:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:4:

Val  Val  Asn  Gly  Ile  Pro  Thr  Xaa  Thr  Asn  Ile  Gly  Xaa  Met  Val  Ser
  1                  5                      10                      15

Leu ( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CANCANTTRC CNTADGG 17

( 2 ) INFORMATION FOR SEQ ID NO:6:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:6:

```
Val Val Asn Gly Ile Pro Thr Arg Thr Asn Ile Gly Trp Met Val Ser
  1               5                  10                  15
Leu Arg Tyr Arg Asn
             20
```

( 2 ) INFORMATION FOR SEQ ID NO:7:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Asn Tyr Met Gly Asn Leu Ser Gln Thr Arg Ser Gly Leu
  1               5                  10
```

( 2 ) INFORMATION FOR SEQ ID NO:8:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Thr Ser Xaa Ser Val Tyr Gly Trp Gly Tyr Thr Gly Leu Ile Asn Tyr
  1               5                  10                  15
Asp Gly Leu Leu
             20
```

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Phe Leu Pro Ser Ser
  1               5
```

( 2 ) INFORMATION FOR SEQ ID NO:10:

( i ) SEQUENCE CHARACTERISTICS:
   ( A ) LENGTH: 32 base pairs
   ( B ) TYPE: nucleic acid
   ( C ) STRANDEDNESS: single
   ( D ) TOPOLOGY: linear ( i i ) MOLECULE TYPE: cDNA ( i x ) FEATURE:
   ( A ) NAME/KEY: miscfeature
   ( B ) LOCATION: 2..7
   ( D ) OTHER INFORMATION: /function="Sal I cleavage site"

( x i ) SEQUENCE DESCRIPTION: SEQ ID NO:10:

GGTCGACTAG GCACTGACTC CGAACAGGAT TC    32

( 2 ) INFORMATION FOR SEQ ID NO:11:

( i ) SEQUENCE CHARACTERISTICS:
   ( A ) LENGTH: 32 base pairs
   ( B ) TYPE: nucleic acid
   ( C ) STRANDEDNESS: single
   ( D ) TOPOLOGY: linear ( i i ) MOLECULE TYPE: cDNA ( i x ) FEATURE:
   ( A ) NAME/KEY: miscfeature
   ( B ) LOCATION: 2..7
   ( D ) OTHER INFORMATION: /function="Sph I cleavage site"

( x i ) SEQUENCE DESCRIPTION: SEQ ID NO:11:

GGCATGCACA GTTGTATTGG TGGGTGCTTC AG    32

PLASMIDS CONTAINING DNA ENCODING THE AMINO ACID SEQUENCE OF TCF-II AND USE THEREOF

FIELD OF THE INVENTION

The present invention relates to plasmids containing DNA encoding the amino acid sequence of a novel glycoprotein derived from human fibroblasts (it is designated as TCF-II hereafter), transformed cells with the plasmids and a production method for a biologically active substance using the transformed cells.

TCF-II in the present invention is useful for pharmaceutical products as a hepatocyte growth factor, a tumor cytotoxic factor, etc. or a biochemical or pharmacological reagent.

BACKGROUND OF THE INVENTION

Interferon-$\beta$ is a representative factor as the biologically active factor, for example, the tumor cytotoxic factor which is produced by human-derived fibroblasts. This is a glycoprotein which is secreted by the fibroblasts, when the cells after cultivation are harvested and stimulated by polyI-poly C or Sendai virus. It has been clarified that the protein has various physiological activities besides its anti-virus or anti-tumor activity. A fibroblast-derived tumor cytotoxic glycoprotein designated as CBF is disclosed in Japanese Patent Laid-Open No. 58-146293. A tumor growth inhibitory factor (INF) with molecular. weight of 35,000~45,000, which is purified from the culture broth of fibroblasts derived from human tissue, is disclosed in Japanese Patent Laid-Open No. 61-33120. Furthermore, a tumor necrosis factor-like substance which is purified from the culture broth of fibroblasts, a fibroblast-derived necrosis factor, FNF, and a biologically active substance with cytotoxic activity, which is produced by animal-derived fibroblasts and has a molecular weight of 40,000 to 60,000 and an isoelectric point value of $5.0\pm0.5$, are disclosed in Japanese Patent Laid-Open No. 61-56131, Japanese Patent Laid-Open No. 61-1872, and Japanese Patent Laid-Open No. 62-103021, respectively. In addition, all the primary amino acid sequence and cDNA encoding the amino acid sequence of a tumor cytotoxic factor, which is obtained from the culture broth of human-derived fibroblasts, with a molecular weight of $36,000\pm1,000$ and an isoelectric point value more than 10.5 are disclosed in Japanese Patent Laid Open No. 64-10998.

DISCLOSURE OF THE INVENTION

The present inventors investigated biologically active substances which are present in culture broth of human-derived fibroblasts and found a glycoprotein with various biological activities, which is different in molecular weight, isoelectric point value, etc. from previously reported substances. A patent application directed to the novel glycoprotein has been filed (PCT/JP 90/00314; International patent published, WO 90/10651; published date, Sep. 20, 1990).

This novel glycoprotein (TCF-II) derived from human fibroblasts is a glycoprotein which is characterized by the following physicochemical properties.

a. Molecular weight (Mw): On SDS-polyacrylamide gel electrophoresis, it shows bands with Mw $74,000\pm2,000$ and $78,000\pm2,000$ under non-reducing conditions, and also shows a common band A with Mw $52,000\pm2,000$ and band B with Mw $30,000\pm2,000$ and band C with Mw $26,000\pm2,000$ under reducing conditions.

b. Isoelectric point value: 7.4 to 8.6.

c. Heat stability: Stable in the heating at 60° C. for 10 min.

d. pH stability: Stable in the range of pH 6 to 9.

e. Glycoprotein: It is adsorbed to a Concanavalin A (Con A)-Sepharose column.

f. Biological activity: It inhibits the growth of KB cells, HeLa cells and L929-C18 cells, but not IMR-90 cells.

g. Reactivity to antibodies: Its cytotoxic activity is not neutralized by anti-T NF, anti-lymphotoxin, and anti-interferon-$\beta$ antibodies.

Furthermore, preferably TCF-II in the present invention has the following N-terminal amino acid sequence and amino acid composition.

h. N-terminal amino acid sequence: The above mentioned band B and band C are subchains of band A, respectively. The N-terminus of band A is blocked. Band B and band C have the same N-terminal amino acid sequence as follows;

Val—Val—Asn—Gly—Ile—Pro—Thr—     (SEQ ID No: 3)

or

Val—Val—Asn—Gly—Ile—Pro—Thr—X—Thr—Asn—Ile—Gly—X—Met—Val—Ser—Leu—     (SEQ ID No: 4)

where X means an unidentified amino acid.

i. Amino acid composition: When it is hydrolyzed with HCl, it shows the following amino acid composition.

| A.A | n mol | mol % |
|---|---|---|
| Asp | 10.375 | 12.97 |
| Glu | 7.750 | 9.69 |
| Ser | 5.000 | 6.25 |
| Gly | 7.250 | 9.06 |
| His | 3.000 | 3.75 |
| Arg | 5.375 | 6.72 |
| Thr | 5.125 | 6.41 |
| Ala | 2.625 | 3.28 |
| Pro | 5.625 | 7.03 |
| Tyr | 3.875 | 4.84 |
| Val | 4.125 | 5.16 |
| Met | 1.875 | 2.34 |
| Cys | ND | — |
| Ile | 5.000 | 6.25 |
| Leu | 4.875 | 6.09 |
| Phe | 2.250 | 2.81 |
| Trp | ND | — |
| Lys | 5.875 | 7.34 |
| Total | 80.000 | 100(99.99) |

Furthermore, the present inventors determined the nucleotide sequence of cDNA encoding the amino acid sequence of TCF-II and described the nucleotide sequence in the above mentioned patent application. The present inventors purified mRNA encoding TCF-II derived from human embryonic fibroblast, IMR-90 cells, cloned the gene and then deduced the amino acid sequence of TCF-II by determination of the nucleotide sequence of the gene, according to the following methods:

(1) Extraction of poly(A)+RNA from IMR-90 cells

Total RNA was prepared by the guanidine thiocyanate-cesium chloride method (Biochemistry 18, 5294–5299 (1979)) from $2 \times 10^8$ IMR-90 cells which were cultured in Dulbecco's modified Eagle medium (DMEM) containing 5% a new born calf serum (NBCS). The IMR-90 cells were suspended in 28 ml of 6 M guanidine thiocyanate solution containing 5 mM sodium citrate, 0.5% Sarkosyl and 0.1M β-mercaptoethanol, and were homogenized. 4 ml of 5.7 M cesium chloride solution containing 0.1M EDTA was put into each polyallomer centrifuge tube. 7 ml of the homogenized solution was overlaid onto the cesium chloride solution and then centrifuged at 35,000 rpm for 16 hours at 20° C., using the 40 Ti rotor of Beckman centrifuge. After centrifugation, the pellets were washed twice with 95% ethanol and dissolved in 200 μl of 10 mM Tris-HCl buffer (pH 7.5) containing 1 mM EDTA by heating at 65° C. for 5 min. The resulting solution was designated as total RNA solution. Poly(A) +RNA was purified from the total RNA by the method of oligo (dT) cellulose-column chromatogaphy. The total RNA solution was loaded on the oligo (dT) cellulose-column which was equilibrated with 10 mM Tris-HCl buffer (pH 7.4) containing 1 mM EDTA, 0.5 M NaCl and 0.05% SDS. The adsorbed fraction on the column was eluted with 10 mM Tris-HCl buffer, pH 7.4, containing 1 mM EDTA and 0.05% SDS. The eluate was designated as poly(A) +RNA solution.

(2) Synthesis of cDNA

Double-stranded cDNA was synthesized by using poly (A)+RNA from (1) as a template and by using cDNA synthesis kit (Pharmacia), and EcoR I adaptor was attached to the cDNA. The method of synthesis was performed according to the protocol of Pharmacia, except for addition of reverse transcriptase (AMV RTase, 40 units/reaction mixture, Life Science) derived from non-sphere disease virus of avian bone marrow at the synthesis of the first strand DNA.

(3) Construction of cDNA library

The cDNA with EcoRI adaptor obtained from (2) was inserted in EcoRI arm (Promega) of phage vector γ gt 10, The cDNA synthesized from 3.3 μg of poly(A) +RNA was dissolved in 150 μl 66 mM Tris-HCl buffer (pH 7.6) containing 1 mM spermidine, 10 mM magnesium chloride, 15 mM dithiothreitol and 0.2 mg/ml of bovine serum albumin (column buffer). 5.2 μl of the above solution was mixed with 1 μg of λ gt 10 EcoR I arm and then precipitated with ethanol Recombinant phage DNA including both λ gt 10 and the cDNA was constructed as follows. The above precipitate was reconstituted in 9 μl of the column buffer and was incubated at 16° C. overnight by adding 1 μl of 10 mM adenesine triphosphate and 1 μl of T4 DNA ligase (350 units/ μl).

(4) Screening of cDNA library (i) Preparation of oligonucleotide probe

For preparation of probe, a mixture of 17 met complementary strand oligonucleotides (384 species mixture) corresponding to the amino acid sequence of Val$^1$ to Pro$^6$ in N-terminal amino acid sequence of TCF-II β-chain was synthesized and labelled 5' terminus with T4 polynucleotide kinase (TAKARA SHUZO Co. Ltd) and [γ-$^{32}$P]ATP (Amersham). This probe is shown as following;

complementary strand used as probe:

(384 species mixture)

3'-CACCACTTACCGTAGGG-5'

```
    G G G C A
    A A   A T
    T T   T     (SEQ ID No: 5)
```

(ii) Screening of recombinant phage

About 500 thousand plaques of phage were obtained by packaging the recombinant phage DNA in vitro which was obtained from (3), using Gigapack Gold (Stratagone) and then by infecting it to E. Col i C600hfl. After adsorption of the plaques to Hybond-N filter (Amersham), they were denatured with alkali, neutralized and baked at 80° C. for 2 hours. Hybridization was performed by the method of Bell et al. (Nature 310, 775–777) (1984)). The first screening was carried out by using the mixture probe which was obtained from (i). One clone which would contain TCF-II cDNA fragment was found in the positive plaques detected by the first screening.

(5) Cloning of full coding region of TCF-II cDNA which can be translated to amino acids N-terminal amino acid sequence of TCF-IIβ-chain and a few internal amino acid sequences (one letter code), (α) NYMGNLSQTRSGL (SEQ ID No.:7) and (β) TSXSVYGWGYTGLINYDGLL (SEQ ID No.: 8) (X: not identified), which were obtained respectively from α- and β-chains of TCF-II by digesting them with lysylendopeptidase, coincided with the corresponding amino acid sequences of one of the human hepatocyte growth factors (hHGFs). Therefore, it was thought that TCF-II is expressed from one of the family of hHGF genes. In regard to hHGF, MIYAZAWA et al. {Biochemical and Biophysical Research Communication 163, 967–973 (1989)) and NAKAMURA et al. (Nature 342, 440–443 (1989)) reported entire nucleotide sequences of hHGF cDNAs, respectively. Comparison of the amino acid sequences deduced from both hHGF cDNAs revealed differences in amino acids at 14 sites in their sequences. From these results, the presence of the family of hHGF genes was suggested. Therefore, on the bases of the identical oligonucleotide sequences of both hHGFs at 5' and 3' non-coding regions, oligonucleotides which were used as primers were chemically synthesized, and screening of TCF-II cDNA was carried out by the method of Polymerase Chain Reaction (PCR). Sal-77 primers, which have a cleavage site of restriction enzyme, Sal I, and Sph2203 primers which have a cleavage site of restriction enzyme, Sph I, were synthesized by DNA synthesizer (Applied System). These primers are shown as following;

Sal-77 primer: 5'-GGTCGACTAGGCACTGACTCCGAACAGGATTC-3'   (SEQ ID No: 10)

Sal I

-continued

Sph2203 primer: 5'-GGCATGCACAGTTGTATTGGTGGGTGCTTCAG-3' (SEQ ID No: 11)
                    Sph I Cloning by PCR method was carried out by following procedures.

(i) PCR

| | |
|---|---|
| cDNA synthesized as described in (2) (dissolved in 150 μl of column buffer) | 1.0 μl |
| 20 μM Sal-77 primer | 2.5 μl |
| 20 μM Sph2203 primer | 2.5 μl |
| 10 × PCR reaction solution (100 mM Tris-HCl, pH 8.3, containing 500 mM KCl, 15 mM MgCl₂ and 0.1% (W/V) gelatin) | 10.0 μl |
| A mixture of each 1.25 mM of dGTP, dATP, dTTP and dCTP | 16.0 μl |
| Ampli Taq (5 units/μl, TAKARA SHUZO) | 0.5 μl |
| Distilled water | 67.5 μl |

After the above solutions were mixed well in a microfuge tube with 0.5 ml volume size and the liquid surface is covered with about 100 μl of mineral oil (Sigma), PCR was carried out by the Quick Thermo System (Nippon Genetics Co. Ltd.). Reaction conditions were shown as follows; after pretreatent at 94° C. for 7 min, a three-step reaction which consists of annealing reaction, at 55° C. for 3 min; polymerase reaction, at 72° C. for 2 min; and denature reaction, at 94° C. for 2 min was repeated 35 times. Then the reaction mixture was treated for 3 min at 55° C., and subsequently for 11 min at 72° C. and then returned to room temperature (Each time includes the altering time of temperature). When a part of the reaction mixture was analyzed by electrophoresis using agarose gel, a DNA fragment with about 2.3 kirobases (Kb), which was thought to be a desired TCF-II cDNA, was obtained. Then, the DNA which was obtained from four tubes containing the above mentioned reaction mixture was precipitated with ethanol and was digested with restriction enzymes, Sal I and Sph I. After an agarose electrophoresis of the digested DNA, the DNA fragment with about 2.3 Kb was recovered by using DE 81 paper (Whatman).

(ii) Subcloning

The cDNA fragment with about 2.3 Kb which was obtained from (i) and was digested with restriction enzymes, Sal I and Sph I, was inserted using ligation kit, (TAKARA SHUZO) into a vector fragment which was obtained by digestion of plasmid vector, pUC18 (Nippon Gene Co. Ltd) with restriction enzymes, Sal I and Sph I, and was transfected into *Esherichia Coli* DH 5 α according to protocol of BRL. More than 20 subclones could be obtained.

(iii) Determination of nucleotide sequence

The nucleotide sequences of the obtained subclones were determined by the dideoxy-method (Sequenase Vet. 2.0 TOYOBO). Incorporation errors of nucleotides caused by Ampi Taq (TAKARA SHUZO) were corrected by analysis of nucleotide sequences of several subclones. The nucleotide sequence of TCF-II cDNA obtained by the above mentioned procedure and the amino acid sequence deduced from the nucleotide sequence are shown in FIG. 1. It consists of 2172 base pairs (bp) from ATG of initiation codon for translation to TAG of termination codon. If the DNA is translated into protein, TCF-II is composed of 723 amino acids. Amino acid sequence from the first methionine (Met$^1$) to the 29th alanine (Ala$^{29}$) residue is presumed as a signal sequence. TCF-II in which two polypeptides consisting of α-chain and β-chain are bound by disulfide bond was found to be initially synthesized as a single chain as shown in FIG. 1.

N-terminal amino acid sequence of α-chain in TCF-II was not detected, because its N-terminus had been blocked. N-terminal amino acid sequence of the β-chain and a few internal amino acid sequences of the α- and β-chains, which had been determined as mentioned above, are shown in FIG. 1. The obtained TCF-II cDNA has similarity in the nucleotide sequence to hHGF which has been found by MIYAZAWA et al. (Biochemical and Biophysical Research Communication 163, 967–973 (1989)). However, the deduced amino acid sequence from TCF-II cDNA deletes five amino acid residues (F-L-P-S-S) (SEQ ID No.: 9) corresponding to Phe$^{162}$ to Ser$^{166}$ in the deduced amino acid sequence from the hHGF cDNA. TCF-II is different in the deletion of five amino acid residues in the coding region from the hHGF. Therefore, the facts revealed that TCF-II cDNA was novel within the family of hHGF genes.

Based on this knowledge concerning the obtained TCF-II cDNA, the present invention is directed towards the insertion of TCF-II cDNA into expression vector and production of TCF-II by recombinant technology (Hereafter, TCF-II produced by recombinant technology is designated as rTCF-II). Therefore, the aim of the present invention is to offer the construction of expression vectors containing DNA encoding the amino acid sequence of TCF-II, transformed cells with the TCF-II expression plasmids, and production method of rTCF-II or recombinant hepatocyte growth factor using the transformed cells.

The present invention was carried out by settlement of such subjects mentioned above. Firstly, the present invention relates to expression plasmid containing DNA encoding the amino acid sequence of TCF-II.

Expression vectors are e.g. pcDNA I (Invitrogen), pMNSM (Tsuchiya et al. Biochemical and Biophysical Research Communication 158, 576–583 (1989)), etc.

A plasmid in the present invention is generally constructed according to the following methods. TCF-II cDNA which is subcloned into pUC18 plasmid (Nippon Gene) as mentioned above is cut out from the plasmid by using restriction enzymes. On the other hand, for example, a plasmid fragment is cut out from expression vector, pcDNA I (Invitrogen) by using restriction enzymes. Then, TCF-II expression plasmid is constructed by ligating both fragments using a ligase and by inserting TCF-II cDNA fragment into the pcDNA I fragment. To cut out TCF-II cDNA, plasmid fragments, etc., various kinds of restriction enzyme which have been well known are able to be used, especially Bam H I, Sph I, etc. are preferable to use as restriction enzymes. T₄ DNA ligase is also preferable as a ligase. Cutting out of plasmid fragments, and their ligations may be carried out according to the methods which have been well known and established. In the present invention, plasmid, pcDTCFdh for TCF-II expression in a large amount, which can achieve rTCF-II expression in a large amount, can be constructed according to the method as shown in FIG. 4.

Mouse DHFR expression plasmid, pAdD26SVpA(3) (Proc. Natl. Acad. Sci. USA 82, 689–693 (1985)) was separately digested with restriction enzymes, EcoR I and BamH I and with restriction enzymes, BamH I and Pst I. After the separately digested plasmids were electrophoresed using ME agarose gel (1%, TAKARA SHUZO), 1.8 kb and 0.5 kb DNA fragments were recovered from each plasmid by using DE 81 paper (Whatman), respectively. Mouse DHFR expression plasmid, pBAdDSV was constructed by mixing both DNA fragments (1.8 kb and 0.5 kb DNAs) with Bluescript SK+ (Stratagene) digested with EcoR I and Pst I, and b7 ligation them using T4 DNA ligase. Plasmid for TCF-II expression in a large amount, pcDTCFdh, was obtained by inserting 2.4 kb DNA fragment, which was obtained from plasmid, pBAdDSV digested with Nae I and blunt-ended with Krenow fragment, into TCF-II expression plasmid (FIG. 2, 6.3 kb) using $T_4$ DNA ligase.

Thus obtained plasmid, pcDTCFdh contains TCF-II expression unit, which consists of cytomegarovirus promotor and TCF-II cDNA locating between the promotor and splicing and polyadenylation sites originated from SV40 early gene, and mouse DHFR expression unit, which consists of adenovirus later promotor and mouse DHFR gene locating between the promotor and polyadenylation site originated from SV40 early gene.

Thus obtained TCF-II expression plasmid is amplified using *Esherichia Coli* (*E. Coli*) and purified from the *E. Coli*. Various kinds of *E. Coli* such as MC1061/P3 etc, which are commercially available, are able to be used. The plasmid is selected and amplified by culturing *E. Coli.* having the plasmid in medium containing ampicillin etc. and then purified from the *E. Coli*. A transformant obtained by transfection of *E. Coli*., MC1061/P3 with the expression plasmid (FIG. 2) in the present invention has been deposited to Fermentation Research Institute, Agency of Industrial Science and Technology as a deposit number, FERM BP-3479.

The present invention also relates to transformed cells which are obtained by tranfection of cells with the obtained TCF-II expression plasmid. Mammalian cells such as Cos-1, CHO, Namalwa, Φ2, NIH 3T3, BHK cells, etc. are preferable to use. The transfection can be carried out according to the ordinarily used methods such as calcium phosphate, DEAE-dextran, lipofectin, electropotation methods, etc.

Furthermore, the present invention relates to producion of rTCF-II by cultivation of thus obtained transformed cells and purification of rTCF-II from the culture broth. The cultivation can be performed according to the method described in WO90/10651. That is, the transformed mammalian cells are grown in the medium with serum or without serum. Dulbecco's modified Eagle medium(DMEM) containing 5% new born calf serum is given as the representative medium. Amino acids, transferin, fatty acids, and hormones such as insulin etc. can be added to the medium if necessary.

The cells are cultured in the medium, and the standing culture using T-flasks etc., the floating culture using microcarrier, and the continuous culture using hollow fiber or ceramic carrier are able to be adapted as culture systems. It is preferable that the culture is carried out in atmosphere with 5% $CO_2$ at 20° to 37° C. as culture conditions and that the medium is exchanged every 2 to 3 days. After the cell density reaches the optimum, the medium is exchanged every 7 to 10 days and the culture broth is collected. The desired glycoprotein is purified from the collected culture broth. The culture broth is concentrated about 10-fold by ultra-filtration (UF) using a membrane with a pore size of Mw 6,000. The desired glycoprotein in the UF concentrate is adsorbed to cation exchange resins and then eluted from the resins with buffers containing 0.3 to 0.6M NaCl. CM Sephadex C-50 (Pharmacia) etc. can be given as the ion exchange resins. The eluted fractions which have a potent hepatocyte growth stimulating activity or cytotoxic activity against mouse L929-C18 cells are collected and subsequently applied to affinity chromatography column for glycoprotein. Con A-sepharose (Pharmacia) is especially suitable to affinity chromatography for the desired glycoprotein. The affinity column is equilibrated with 0.05M Tris-HCl buffer, pH 7.0, containing 0.5M NaCl and then the collected active fraction mentioned above is applied to the column. After washing the column with the equlltbration buffer, the active material is eluted from the column with an elution buffer containing carbohydrate corresponding to carbohydrate chain of the glycoprotein adsorbed to the column. When the above mentioned Con A-sepharose is used, the active material is eluted with the buffer containing α-methyl-D-mannopyranoside. The eluted active fraction is dialysed against water and then lyophilized. The lyophilized active material is reconstituted with 0.05M Tris-HCl, pH 6.0 to 7.0, containing 0.2M NaCl and is further purified on HPLC using a column packed with strong cation exchange resins. Mono S column (Pharmacia) is especially suitable as a column with strong cation exchange resins for HPLC. Elution of the active material from Mono S column is carried out by a linear gradient of 0 to 1.0M NaCl and the active fractions are collected. rTCF-II is eluted at NaCl concentration of 0.6 to 0.9 M. The obtained active fraction is further purified on an affinity chromatography using heparin-sepharose (Pharmacia). Elution of the active material from heparin-sepharose column is carried out by a linear gradient of 0.3 to 2.0M NaCl and the desired material is eluted at NaCl concentration of 1.0 to 1.5M. Subsequently, assay for hepatocyte growth stimulating activity of rTCF-II is mentioned below.

Hepatocytes were separated from Wister male rats by the method of Segren (Method in Cell Biology, Vol. 13, P 29. Academic Press, New York, 1976). The obtained hepatocytes were seeded into each well in 24-well plastic plates (Falcon) at a cell density of $8.8 \times 10^4$ cells/0.5 ml/well and cultured under the presence of 5% $CO_2$ at 37° C. William E culture medium (Flow Laboratory) supplemented with 10% new born calf serum (Hyclone), 10 μM dexamethasone, 100 u/ml penicillin and 100 μg/ml streptomycin was used as a culture medium (abbreviated below as basal culture medium). After incubation at 37° C. for 24 hours, the culture medium was exchanged with the basal culture medium containing test samples. After the hepatocytes were further cultured for 24 hours, the culture broth was exchanged with the basal culture medium containing 4 μCi/ml (86 Ci/m mol) of $^3$H-thymidine (Amersham). After cultivation-for 2 hours, DNA synthesis of the cells was determined. In the labelling of the cells with $^3$H-thymidine, the incorporated radioactivities (dpm) were defined as the difference of the radioactivities (dpm) which were measured between the presence and absence of 10 mM hydroxyurea on each test sample. After the cell's were washed twice with cold PBS, 10% perchloric acid and 95% ethanol, respectively and air-dried, the cells were solubilized n 0.8 ml of 10% SDS containing 10 mM MgCl$_2$ followed by determination of radioactivities using a liquid scintillation counter.

Representative hepatocyte growth stimulating activity of rTCF is shown in Table 1.

TABLE 1

| Sample | Concentration (ng/ml) | Hepatocyte growth stimulating activity (dpm/well × 10$^{-3}$) |
|---|---|---|
| No addition | — | 21.7 ± 9.2 |
| hEGF | 20 | 239.3 ± 7.2 |
| rTCF-II | 1 | 93.7 ± 29.7 |
|  | 10 | 378.5 ± 93.5 |
|  | 100 | 467.4 ± 77.3 |

(n = 4)

hEGF (WAKUNAGA Pharmaceutical Co.) was used as a positive control for hepatocyte growth stimulating activity. The results in Table 1 indicate that rTCF-II is stronger in hepatocyte growth stimulating activity than hEGF. rTCF-II in the present invention is useful as a hepatocyte growth factor, an anti-tumor factor, a leukemia differentiation inducing factor and an endothelial cell growth factor.

BRIEF DESCRIPTION OF THE DRAWINGS

FIG. 1a, FIG. 1b, amd FIG. 1c show all the primary amlno acid sequence of TCF-II and (SEQ ID No:1) nucleotide sequence of DNA encoding the amino acid sequence (SEQ ID No:2)

EXAMPLES

EXAMPLE 1

(1) Construction of TCF-II expression plasmid

Figure 2:
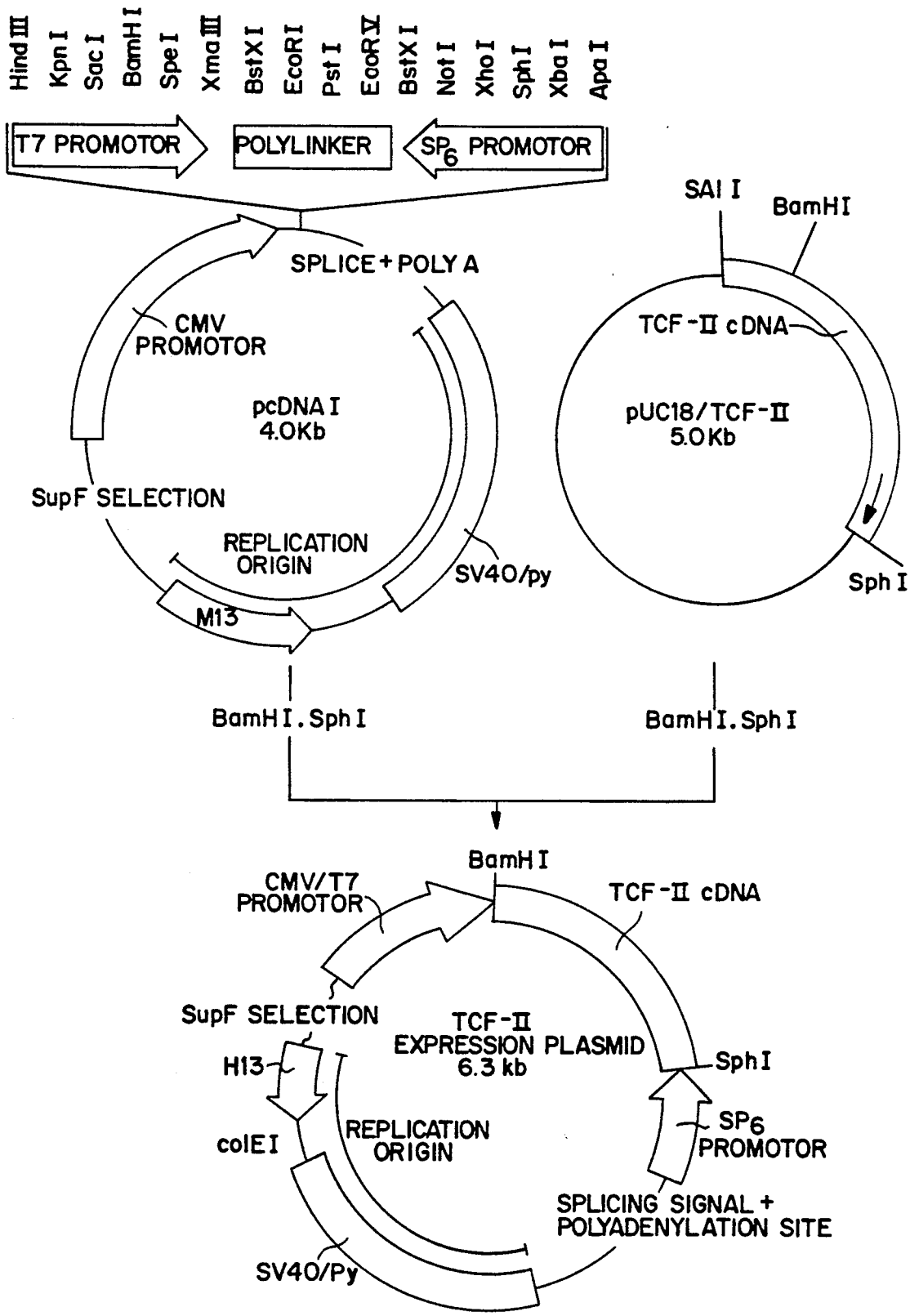
FIG. 2 shows schematic representation of the method of construction of TCF-II expression plasmid in the present invention.

TCF-II cDNA (FIG. 1), which is subcloned into pUC 18 plasmid (Nippon Gene) as shown FIG. 2, and DNA fragment of pcDNA I expression vector(Invitrogen) were cut out by the following restriction enzyme treatments and their DNA fragments were obtained.

1 μg of pUC18 plasmid, which has an insertion of TCF-II cDNA, and 1 μg of pcDNA I plasmid were separately dissolved in 10 μl of 20 mM Tris-HClbuffer, pH 8.5, containing 10 mM MgCl$_2$, 1 mM dithiothreitol and 100 mM KCl. The resulted solutions were digested with each one unit of restriction enzymes, BamH I and Sph I at 37° C. for one hour. After the digestions, TCF-II cDNA fragment with about 2.3 kb and pcDNA I fragment with about 4.0 kb were separated by ME agarose gel (1%, TAKARA SHUZO) electrophoresis and were recovered by using DE81 paper (Whatman), respectively.

Subsequently, TCF-II cDNA fragment was inserted into pcDNA I fragment by the following reactions.

100 ng of TCF-II cDNA fragment and 50 ng of pcDNA I fragment were dissolved in 10 μl of 60 mM Tris-HCl buffer, pH 7.6, containing 1 mM ATP, 1 mM spermidine, 10 mM MgCl$_2$ and 15 mM DTT and subsequently ligated by incubating the mixture with 300 units of T$_4$ DNA ligase at 15° C. overnight.

Subsequently, a transformant having TCF-II cDNA expression plasmid was obtained by transfection of E. Coli. , MC1061/P3 with the above mentioned reaction solution according to the conventionally used method.

This transformant has been deposited to Fermentation Research Institute; Agency of Industrial Science and Technology as a deposit number, FERM BP-3479. The constructed TCF-II expression plasmid is shown in FIG. 2.

(2) Preparation and Purification of TCF-II Expression Plasmid

The transformed E. Coli. mentioned above was cultured in one liter of L-medium containing 25 μg/ml ampicillin and was further cultured overnight by adding chloramphenicol to the culture at a final concentration of 170 μg/ml when OD.660 nm of the culture broth reached 0.8. TCF-II expression plasmid was purified by CsCl density gradient ultracentrifugation after treatments of the plasmid with alkali and polyethyleneglycol according to the method of Maniatis et al.(Molecular cloning 2nd edition).

(3) Transformation of Mammalian Cells with TCF-II Expression Plasmid

According to the method of Parker et al. (J. Virology 31, 360–369 (1979)), TCF-II expression plasmid was transfected into Cos-I cells by calcium phosphate method. As a negative control, pcDNA I alone was transfected into Cos-I cells in the same way.

(4) Confirmation of rTCF-II Expression

Figure 3:
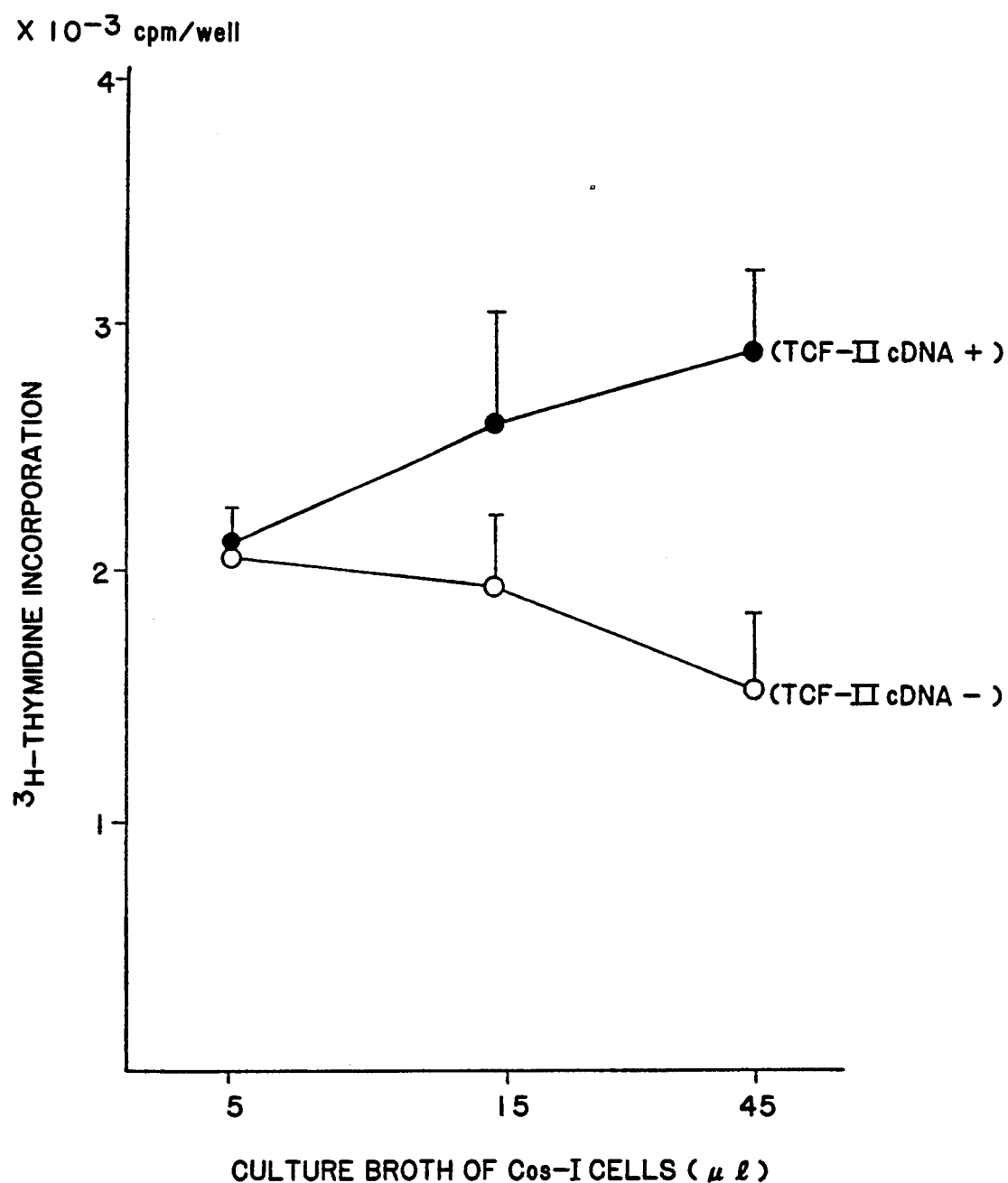
FIG. 3 shows the expression of TCF-II cDNA. In the figure, — — and — ● — show HGF activities in the culture broth of Cos-1 cells without TCF-II cDNA and with TCF-II cDNA, respectively.
Figure 4:
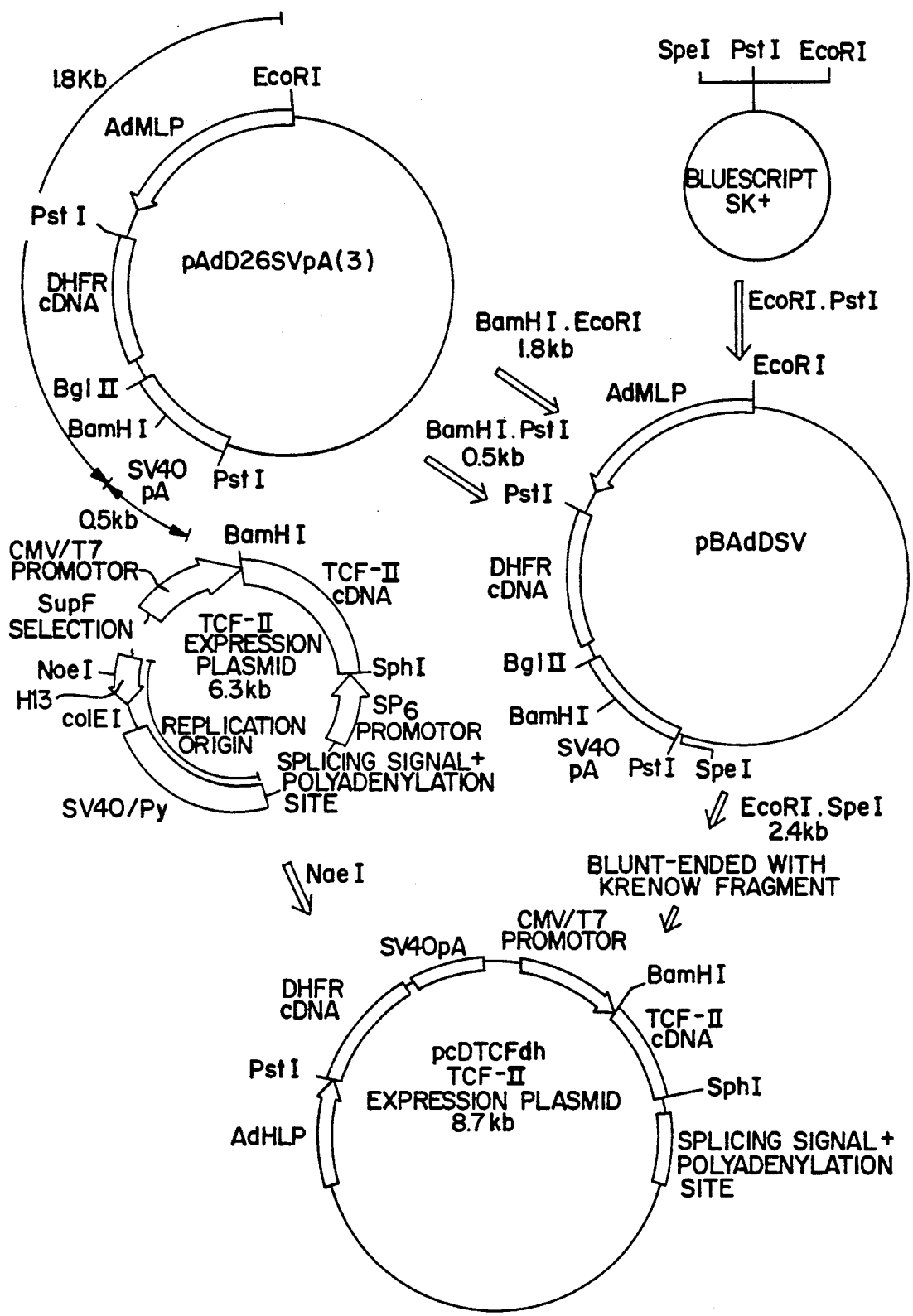
FIG. 4 shows schematic representation of the method of construction of plasmid for TCF-II expression in a large amount.

To confirm expression of biologically active rTCF-II, rat hepatocyte growth stimulating activity, which was used as an indicator for expression of rTCF-II, in the culture supernatant of Cos-I cells at 72 hours incubation after transformation of the cells with TCF-II expression plasmid was investigated. DNA synthesis of rat hepatocytes was measured by incorporation of $^3$H-thymidine into DNA according to the method of Gohda et al. (J. Clin. Invest. 81, 414–419 (1988)). The results are shown in FIG. 3. As shown in FIG. 3, rat hepatocyte growth stimulating activity was detected in the culture supernatant of Cos-I cells at 72 hours incubation after transformation of the cells with TCF-II expression plasmid and thereby the expression of rTCF-II was confirmed. Rat hepatocyte growth stimulating activity was not detected in the culture supernatant of Cos-I cells transfected pcDNA I vector only.

EXAMPLE 2

(1) Construction of plasmid for TCF-II expression in a large amount

Mouse DHFR expression plasmid, pAD265VpA(3) (Proc. Natl. Acad. Sci. USA 82, 689–693 (1985)) was separately digested with restriction enzymes, EcoR I and BamH I, and with restriction enzymes, BamH I and Pst I. After the separately digested plasmids were electrophoresed using ME agarose gel (1%, TAKARA SHUZO), 1.8 kb DNA and 0.5 kb DNA fragments were recovered from each plasmid by using DE 81 paper (Whatman), respectively. Mouse DHFR expression plasmid, pBAdDSV was constructed by mixing the both DNA fragments (1.8 kb and 0.5 kb DNAs) with Bluescript SK+ (Stratagene) digested with restriction enzymes, EcoR I and Pst I and by ligating them using $T_4$ DNA ligase according to the method as shown in EXAMPLE 1.

pBAdDSV plasmid was digested with restriction enzymes, EcoR I and Spe I. After separation by electrophoresis, the digested fragment (EcoR I - Spe I, 2.4 kb) was recovered by using DE 81 paper (Whatman) and was blunt-ended with Krenow fragment. Plasmid, pcDTCFdh for TCF-II expression in a large amount was obtained by inserting the 2.4 kb DNA fragment from the plasmid, pBAdDSV into TCF-II expression plasmid (FIG. 2, 6.3 kb), which was digested with Nae I, using $T_4$ DNA ligase. Thus obtained plasmid, pcDTCFdh contains TCF-II expression unit, which is consisting of cytomegarovirus promotor and TCF-II cDNA locating between the promotor and splicing and polyadenylation sites originated from SV40 early gene, and mouse DHFR expression unit, which consists of adenovirus late promotor and mouse DHFR gene locating between the promotor and polyadenylation site originated from SV40 early gene.

(2) Transformation of Namalwa Cells with TCF-II Expression Plasmid and Expression of TCF-II Gene Namalwa cells, ATCC CRL 1432, was transformed with plasmid, pcDTCFdh for TCF-II expression in a large amount by lipofectin method (Focus 11 (2), 37 (1989)) as described below.

The plasmid DNA solution was prepared by dissolving 10 μg of the plasmid, pcDTCFdh and 1 μg of a plasmid, pMCIneo in 10 μl of TE buffer (10 mM Tris, 1 mM EDTA, pH 7.5) and by adding 1.5 ml of OPTI-MEM (GIBCO) to this DNA solution. Lipofectin solution was prepared by adding 0.1 ml of lipofectin (1 μg/ml, BRL) to 1.4 ml of OPTI-MEM according to the protocol of BRL. Namalwa cells, $1 \times 10^7$ cells, were suspended in 0.3 ml of OPTI-MEM. 1.5 ml of lipofectin solution and 0.3 ml of Namalwa cell suspension were added to 1.5 ml of the above mentioned plasmid DNA solution. After mixing them gently by pipetting, a mixture was transferred to T-flask (25 cm$^2$, SUMITOMO BAKELITE Co.) and incubated in $CO_2$ incubator for 4 hours followed by addition of 7 ml of culture medium (RPMI 1640 containing 10% FCS) and incubation overnight. The cells were incubated for 3 days by exchanging the culture broth with culture medium and was further incubated for 2 weeks by exchanging the culture broth with culture medium containing 500 μg/ml G418 (SIGMA). G418 resistant cells obtained from the above culture were suspended in α-MEM (GIBCO) containing 50 nM methotrexate (MTX) and 10% dialysed FCS, inoculated into each well in 96-well microplates at a cell density of 5,000 cells/well and incubated for 2 weeks. TCF-II high producing strains among the obtained MTX resistant strains were screened by an ELISA. A TCF-II high producing clone, $G_2H_3C_2$ was obtained by cloning the obtained TCF-II high producing cells using RPMI 1640 medium containing 10% FCS and 10% hybridoma cloning factor (Origen)by limiting dilution method, and by screening TCF-II high producing clones by an ELISA. The productivity of TCF-II in the culture supernatant of this clone was about 1.0 mg/l. This clone, $G_2H_3C_2$ has been deposited to Fermentation Research Institute; Agency of Industrial Science and Technology as a deposit number, FERM E)P-3480.

(3) Purification of rTCF-II

1) Culture of transformed Namalwa cells ($G_2H_3C_2$)

The transformed Namalwa cells were inoculated at a cell density of $4 \times 10^5$ cells/ml in 2.5l of RPMI 1640 medium containing 5% calf serum (CS) and were incubated at 37° C. 20l of culture broth was obtained by fed-batch culture method in which 2.5 l of the same medium was added every two days incubation at 37° C.

2) Assay for rTCF-II activity

Mouse L929 cells (ATCC CCL1) were subcloned and a subclone, L929-C18 with the highest sensitivity to TCF-II was selected. L929-C18 cells were grown to conflence in Dulbecco's modified Eagle medium (DMEM) containing 10% FCS, and then the cells were harvested by trypsin treatment. The cells were suspended at a cell density of $6 \times 10^5$ cells/ml in DMEM containing 10% FCS and 1 μg/ml actinomycin D. 50 μl of DMEM which was prepared in the same way as the cell suspension was added to each well in 96-well microplates (Falcon, 3072) and 50 μl of the sample solution, which was prepared by dissolving or diluting the sample containing rTCF-II in the present invention in or with the same DMEM, was added to the first dilution well. Both were mixed well and 50 μl of the mixture was subsequently added to the second dilution well and mixed well. A serially diluted sample was prepared by repeating the above procedures. 50 μl of the cell suspension was inoculated into each well containing a serially diluted sample and the cell culture was carried out at 37° C. for 2 days in a $CO_2$ incubator. After incubation, the medium was removed gently and the cells were washed twice with physiological saline. The viable cells which adhere to each well were fixed and stained by addition of 50 μl of 0.5% crystal violet in a mixture of methanol and water (1 : 4) to each well. Each well was washed with distilled Water and air-dried. The crystal violet in each well was extracted with Sorenson's buffer(a mixture of 6.1 ml of 0.1 M disodium citrate, 3.9 ml of 0.1 N HC1 and 10 ml of ethanol). Absorbance of the extracts at 570 nm was measured by a microtiter spectrophotometer.

Units of TCF-II (u/ml) were defined as the dilution ratio given 50 % cell death.

3) Purification of rTCF-II

Figure 5:
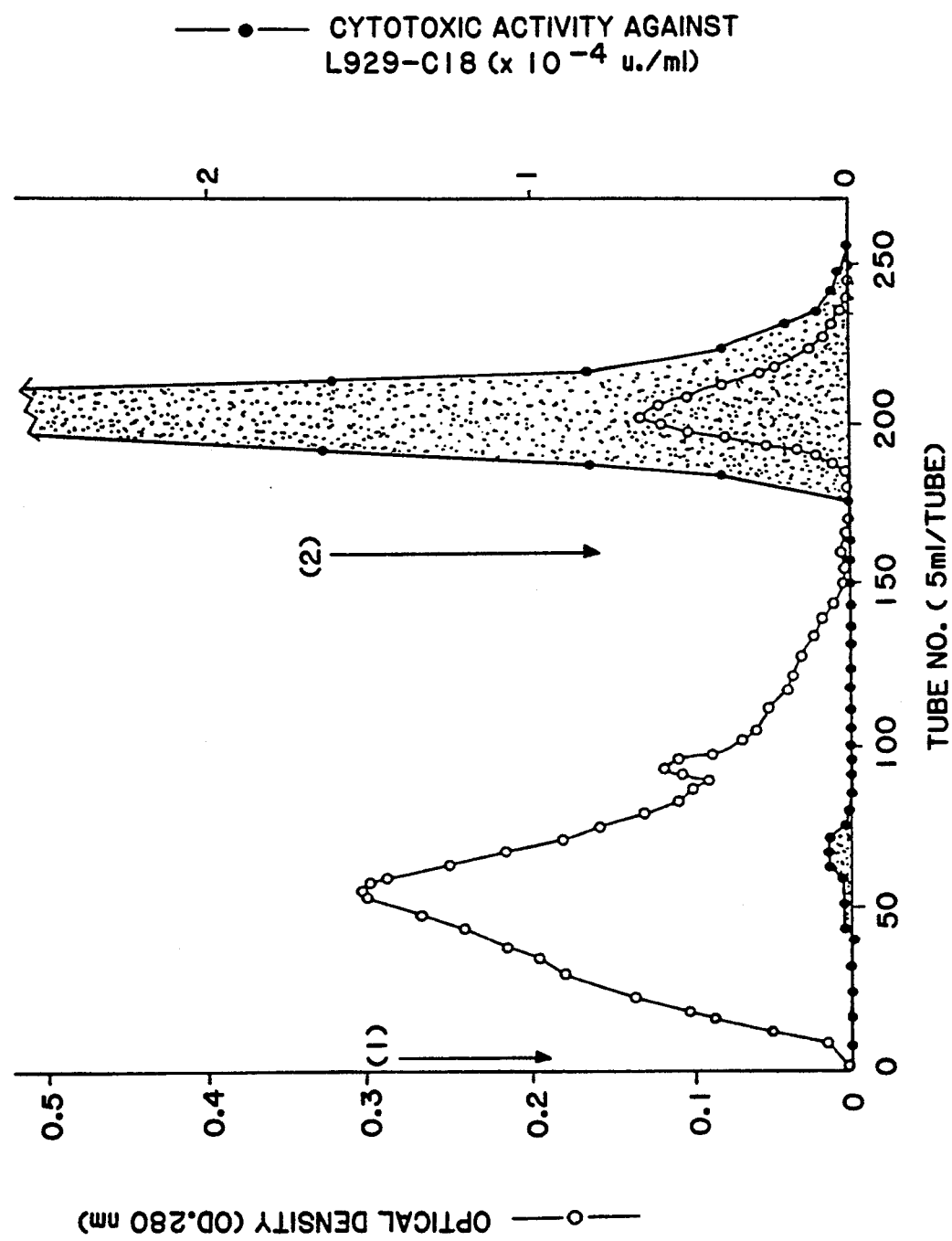
FIG. 5 shows CM sephadex C-50 column chromatography of the culture broth (containing 5% CS) of transformed Namalwa cells with the TCF-II expression plasmid. In the figure, (1) and (2) show the fractions eluted with 0.05M Tris-HCl buffer (pH 6.8 to 7.0) containing 0.3M NaCl and 0.01% Tween 20, and with 0.05M Tris-HCl buffer (pH 7.0) containing 0.6M NaCl and 0.01% Tween 20, respectively. — — and — ● — show optical density at 280 nm (OD. 280 nm) and cytotoxic activity against L929-C18 cells, respectively.

The culture broth, 20 l, described in 1) was adjusted pH to 6.2 to 7.0. 1.5 kg of wet weight of CM Sephadex C-50 , which was equilibrated with 0.05M Tris-HC1 buffer, pH 7.0, was added to the culture broth mentioned above and the aimed material was adsorbed to the resins by gently stirring at 4° C. for 24 hours in pH range of 6.5 to 7.0. After the adsorption, the resins were collected by filtering through a Whatman No. 2 filter paper on Buchuner funnel. The collected resins were washed with 0.05M Tris-HC1 buffer, pH 7.0. Approximately 1,500 g of the washed resins was packed into a column (Φ7×40 cm), and the column was eluted with 0.05M Tris-HC1 buffer, pH 7.0, containing 0.01% Tween 20 and 0.3M NaCl. Elution of protein was monitored by absorbance at 280 nm. When protein was eluted almost completely, the column was further eluted with a salt concentration of 0.6M NaCl in the same buffer. Cytotoxic activity against L929-C18 cells in each fraction was determined. The obtained elution profile was shown in FIG. 5. The fraction which was eluted at a salt concentration of 0.6M NaCl showed a potent cytotoxic activity. This fraction was designated as rTCF-II fraction. Then, Con A-sepharose CL-6B (Pharmacia) was equilibrated with 0.05M Tris-HCl buffer, pH 7.0, containing 0.5M NaCl, 1 mM $CaCl_2$ and 1 mM $MgCl_2$ and the gel was packed into the column (Φ2.5×8 cm).

The column was washed well with the same buffer. rTCF-II fraction (ph 7.0) obtained from CM Sephadex C-50 chromatography was loaded on the column. After the column was washed again with 0.05M Tris-HCl buffer, pH 7.0, containing 0.5 M NaCl with 10 times volume of the column bed, the desired material was eluted with 0.05M Tris-HCl buffer, pH 7.0, containing 0.5M NaCl and 0.3M α-methyl-D-mannopyranoside at a flow rate of 70 ml/hr.

Figure 6:
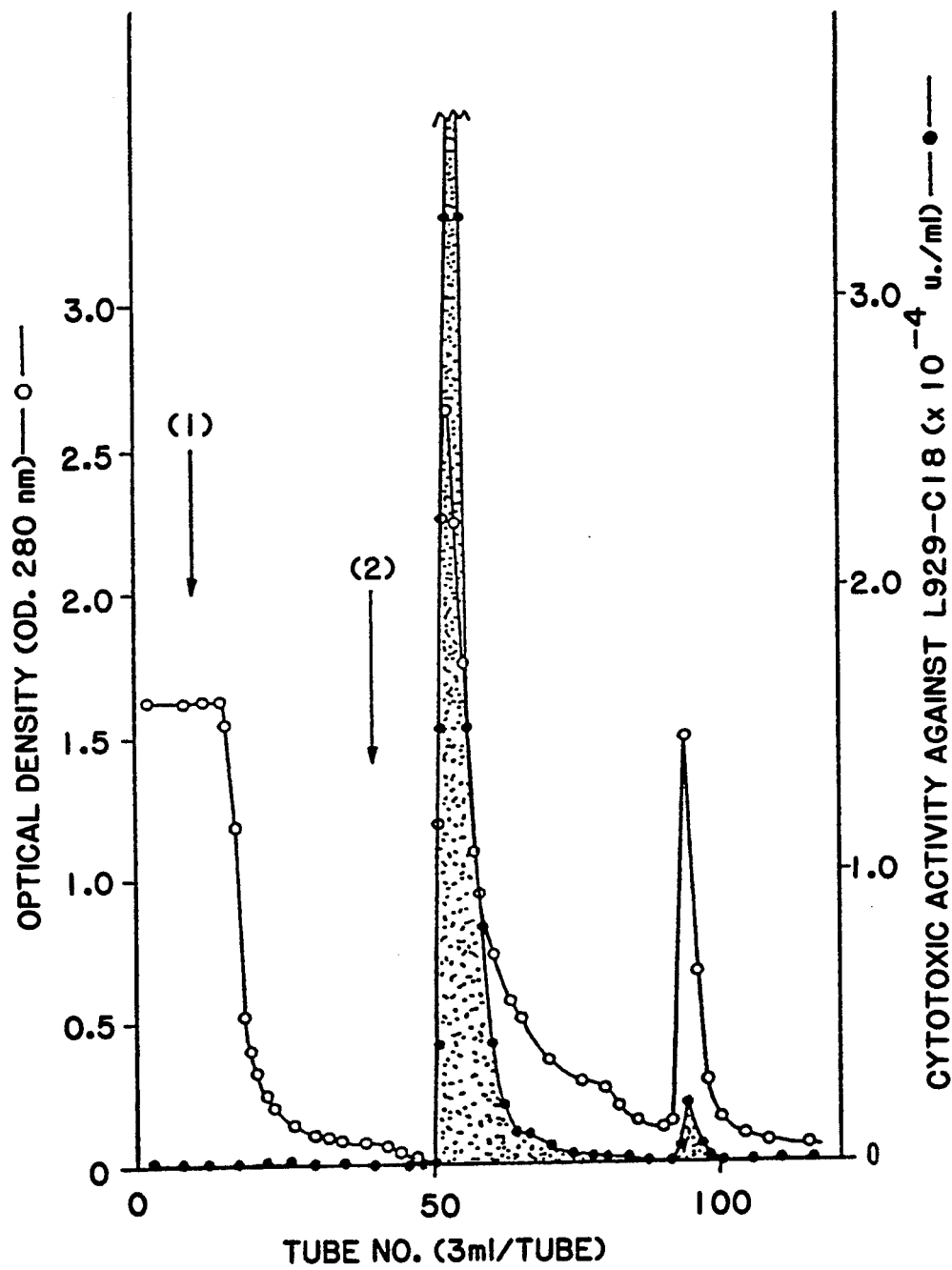
FIG. 6 shows Con A-sepharose CL-6B affinity chromatography of the eluted rTCF-II fraction ( fraction eluted at 0.6M NaCl) from CM sephadex C-50 chromatography. In the figure, (1) and (2) show the fractions eluted with 0.05M Tris-HCl buffer (pH 7.0) containing 0.5M NaCl and 0.05M Tris-HCl buffer (pH 7.0) containing 0.5M NaCl, 0.01% Tween 20 and 0.3M α-methyl-D-mannopyranoside, respectively. —●— and — — show optical density (OD. 280 rim) and cytotoxic activity against Lg29-C18 cells, respectively.
Figure 7:
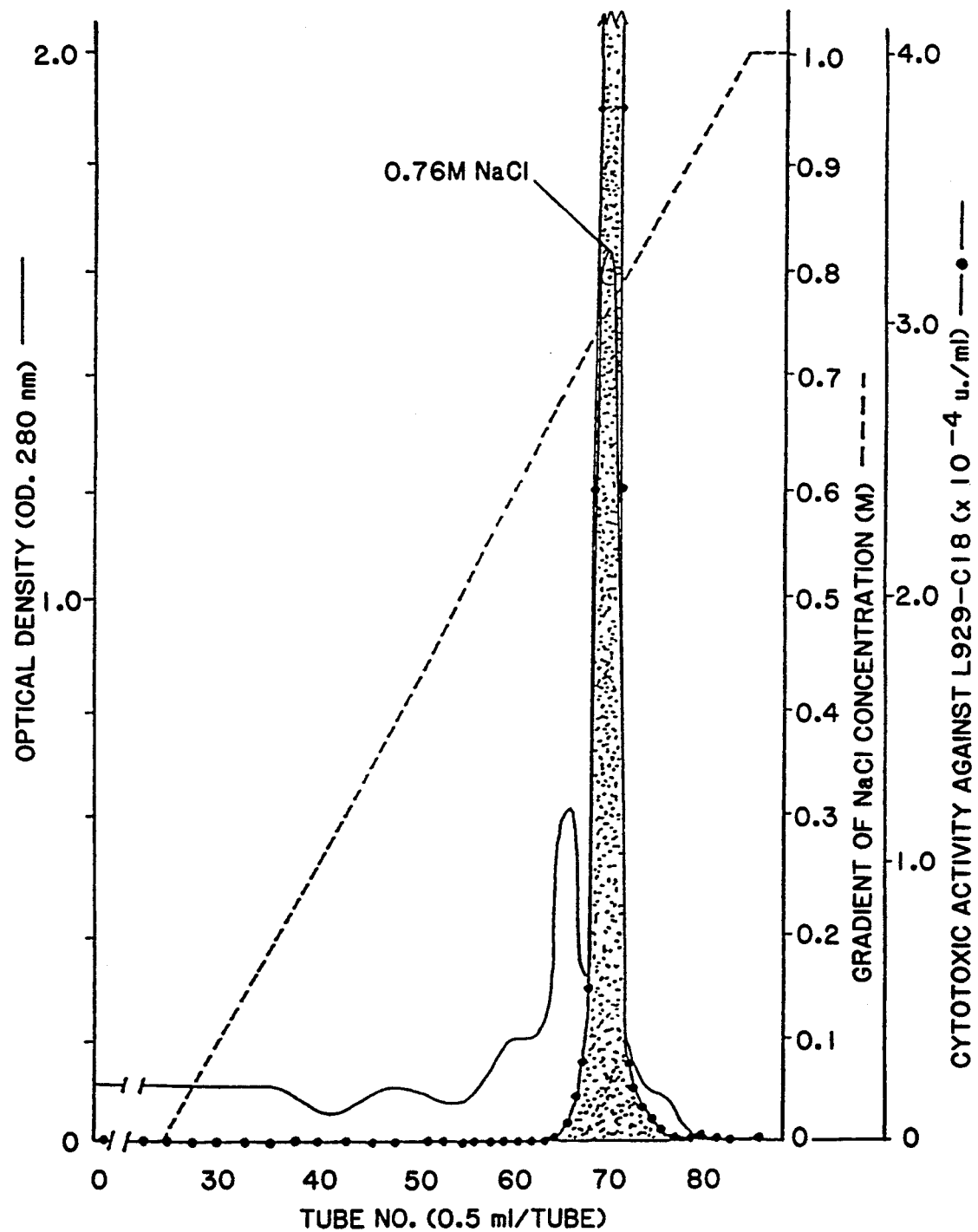
FIG. 7 shows Mono S-HPLC of the eluted rTCF-II fraction from Con A-sepharose CL-6B affinity chromatography. In the figure, — , — ● — and - - - - show optical density (OD. 280 nm), cytotoxic activity/against L929-C18 cells and a linear gradient of NaCl concentration, respectively.
Figure 8:
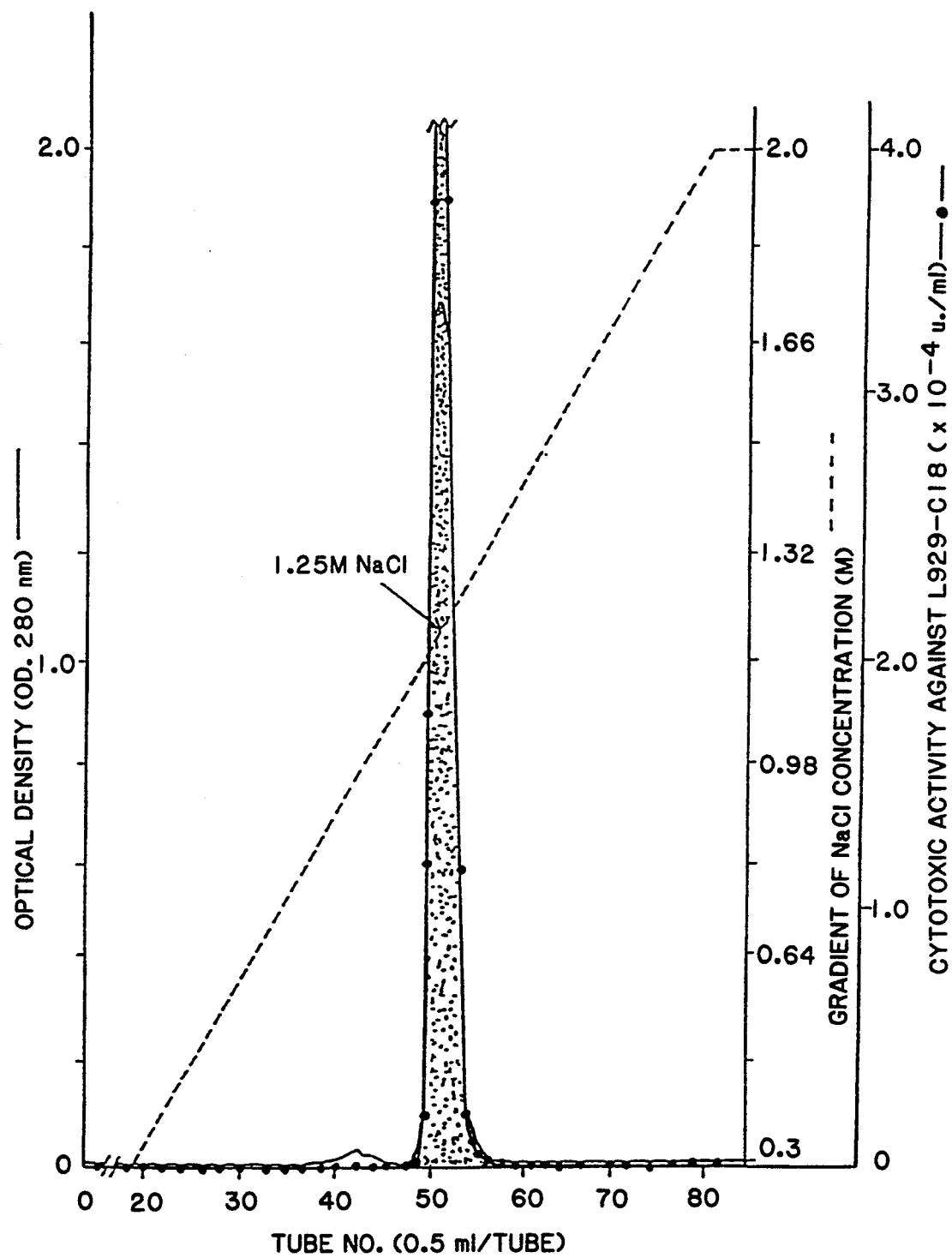
FIG. 8 shows heparin-HPLC of the eluted rTCF-II fraction from Mono S-HPLC. in the figure, —,— ● — and show optical density (OD. 280 rim), cytotoxic activity and a linear gradient of NaCl concentration, respectively.

Elution of protein was monitored by optical absorbance at 280 nm and cytotoxic activity in each fraction was determined. The obtained elution profile was shown in FIG. 6. The fractions which were eluted firstly were collected. The collected fraction was diluted with 0.01M phosphate buffer, pH 7.0 to give a final NaCl concentration of below 0.3M. The diluted fraction, which was adjusted pH to 6.5 to 7.0, was loaded on Mono S column (Pharmacia) for HPLC which was equilibrated with 0.01M phosphate buffer, pH 7.0, containing 0.01% Tween 20 . After loading, the column was washed with 0.01M phosphate buffer, pH 7.0, containing 0.01% Tween 20 for 20 min at a flow rate of 0.5 ml/min, and then eluted with a linear gradient from 0 to 1.0M NaCl for 60 min at a flow rate of 0.5 ml/min. The obtained elution profile was shown in FIG. 7. The active fraction was eluted at 0.76 M NaCl. To increase the purity, the collected active fraction was diluted as mentioned above and was loaded again on Mono S column. Elution was carried out again by the gradient from 0 to 1.0 M NaCl. The active fractions were collected. The obtained active fraction, which was diluted with 10 mM Tris-HC1 buffer, pH 7.5, containing 0.01% Tween 20 to give a final NaCl concentration of 0.3M, was loaded on heparin column for HPLC (TOSO), which was equilibrated with 10 mM Tris-HCl buffer, pH 7.5, containing 0.3M NaCl and 0.01% Tween 20 . After loading, the column was washed with 10 mM Tris-HCl buffer, pH 7.5, containing 0.3M NaCl and 0.01% Tween 20 for 20 min at a flow rate of 0.5 ml/min. The active material was eluted from the column with a linear gradient from 0.3 to 2.0 M NaCl in the same buffer for 60 min at a flow rate of 0.5 ml/min. The obtained elution profile was shown in FIG. 8.

Thus, the purified rTCF-II was obtained. 11.6 mg of the active protein was obtained from 20 l of culture broth. A specific activity of the purified protein for cytotoxic activity was about $5.3 \times 10^6$ units/mg protein.

(4) Physicochemical properties of rTCF-II

Figure 9:
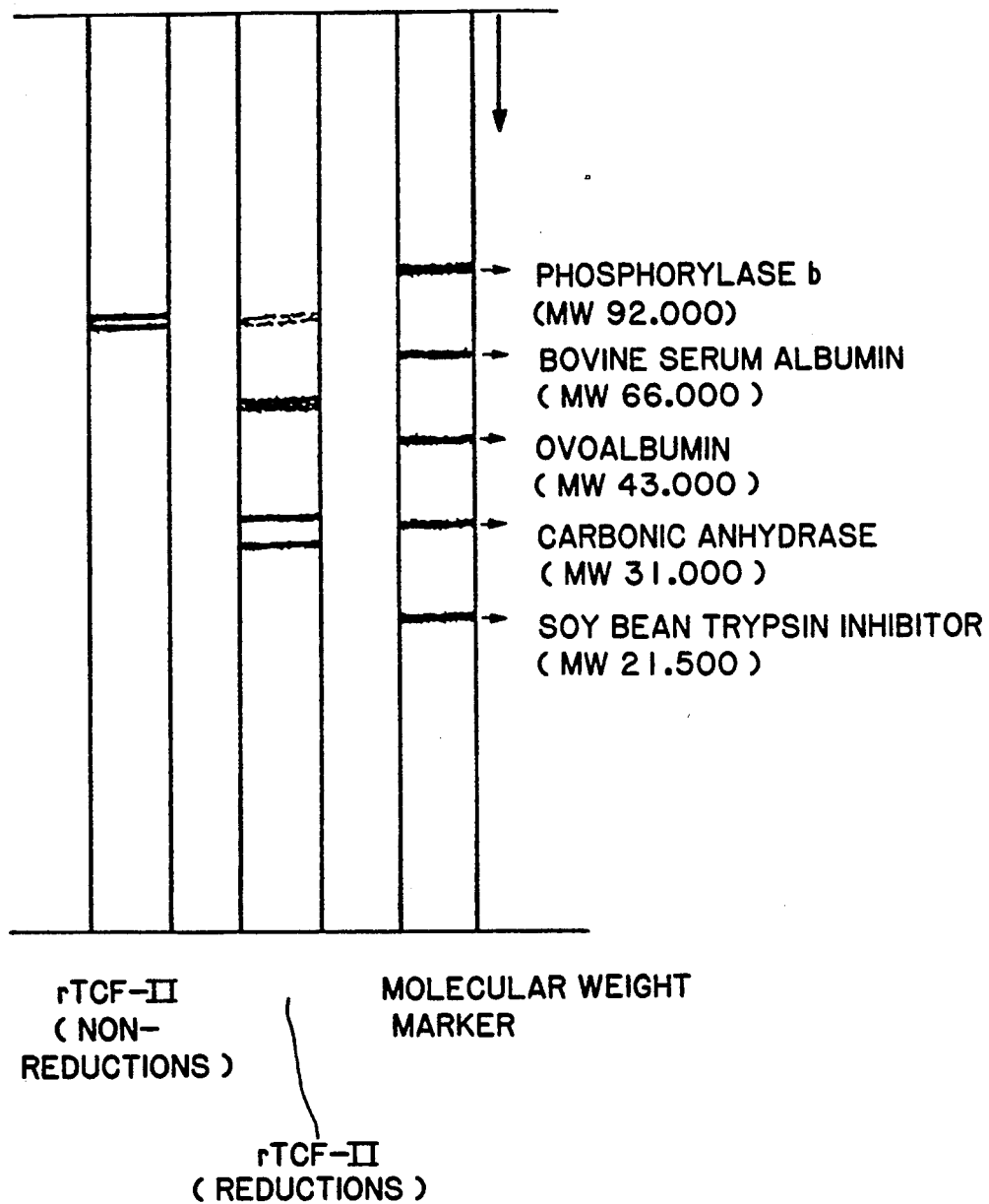
FIG. 9 shows SDS-polyacrylamide gel electrophoresis of purified rTCF-II (under non-reducing and reducing conditions).

Physicochemical properties of rTCF-iI obtained by the above mentioned procedures are shown as follows;

① Determination of molecular weight on SDS-polyacrylamide gel electrophoresis Molecular weight of rTCF-II was determined by electrophoresis using polyacryl amide gel containing 0.1% SDS. SDS-electrophoresis pattern of rTCF-II was shown in FIG. 9. rTCF-II showed two adjacent bands with 78,000±2,000 and 74,000±2,000 under non-reducing conditions. Under reducing conditions, rTCF-II separated into three polypeptide bands composed of a common band A with MW 52,000±2,000, band B with MW 30,000±2,000 and band C with MW 26,000±2,000.

② Isoelectric point value

Isoelectric point values of rTCF-II were determined as 7.4 to 8.6 by isoelectric focussing using LKB electrophoresis equipment and Phast Gel IEF3-9.

③ Heat stability rTCF-II was dissolved in 0.1M Tris-HC1 buffer, pH 7.5, containing 0.01% Tween 20 at a concentration of 600 u/ml. rTCF-II solution was allowed to stand for 10 min at 25, 35, 50, 60, 70, 80, 90 and 95° C . The residual activity after heat treatment at each temperature was estimated as relative activity (%) against the activity (100%) of the control which was allowed to stand at 25° C.

rTCF-II was stable till 60° C.

④ pH stability

Each buffer as shown in Table 2, which contains 0.01% Tween 20 , was prepared. rTCF was dissolved in each buffer (Table 2) at a final concentration of 600 u/ml and was allowed to stand at 37° C. or 1 hour. The residual cytotoxic activity was estimated as relative activity (%) against the activity (100 %) of the control which was allowed to stand at pH 8.0 at room temperature for 1 hour.

rTCF-II was stable in the range of pH 6.0 to 9.0.

TABLE 2

| | Buffers |
|---|---|
| pH 1~3 | 1/10 M Glycine - HCl |
| pH 4~6 | 1/10 M Acetate buffer |
| pH 7~8 | 1/10 M Tris - HCl |
| pH 9~12 | 1/10 M Glycine - NaOH |

(5) N-terminal amino acid sequence

100 μg of rTCF-II was reduced, and three polypeptides, A with MW 52,000, B with 32,000, and C with MW 28,000 were separated by the electroblot method. N-terminal amino acid sequence of each polypeptide was analyzed using the Applied Biosystems 477 A Protein Sequencer. N-terminal amino acid sequence of polypeptide A could not be determined because its N-terminus had been blocked. Polypeptides, B and C had the same N-terminal amino acid sequence as follows;

Val—Val—Asn—Gly—Ile—Pro—Thr—Arg—Thr—Asn—Ile—Gly—Trp—Met—Val—Ser—Leu—Arg—Tyr—Arg—
1           5                        10                          15                        20
Asn

Since polypeptide B and C show the same N-terminal amino acid sequence, rTCF-II appears to have a heterodimer structure in which polypeptide A with MW 52,000 is bound to polypeptide B with MW 32,000 or to polypeptide C with MW 28,000 by disulfide bridge.

(5) Biological activity of rTCF-II

1) Tumor cytotoxic activity

A human tumor cell line, KB and mouse tumor cell lines, Sarcoma 180 and Meth A sarcoma were used as target cells. Human embryonic lung fibroblast, IMR-90 cells were also used as normal cells. KB and Sarcoma 180 cells were suspended at a cell density of $1 \times 10^4$ cells/ml in DMEM containing 10% FCS. Meth A sarcoma was suspended at a cell density of $1 \times 10^4$/ml in RPMI 1640 containing 10 FCS. Normal cells IMR -90 were suspended at a cell density of $1 \times 10^5$ cells/ml in DMEM containing 10% FCS. 50 μl of each cell suspension was added to each well in flat bottomed 96-well microplates (Falcon, 3072).

rTCF-II was dissolved in DMEM containing 10% FCS for KB, Sarcoma 180 and IMR-90 cells, and in RPMI-1640 containing 10% FCS for Meth A sarcoma cells. A serially diluted rTCF-II solution was prepared by diluting the above rTCF-II solution with DMEM or RPMI-1640 with 10% FCS. 50 μl of a serially diluted rTCF-II solution was added to each well containing 50 μl of each cell suspension to give final rTCF-II concentrations of 0, 2, 4, 8, 16, 31, 62, 125, 250, 500 and 1000 ng/ml. After mixing well, the plates were incubated in $CO_2$ incubator at 37° C. for 4 days.

In regard to each cell line, viable cell numbers in each well were counted using a heamacytometer. The viable cell numbers were expressed as mean of duplicate experiments.

$$\text{Cytotoxic activity(\%)} = \frac{\text{Average viable cell numbers in control (cells/ml)} - \text{Average viable cell numbers in rTCFF-II added group (cells/ml)}}{\text{Average viable cell numbers in control (cells/ml)}} \times 100$$

Figure 10:
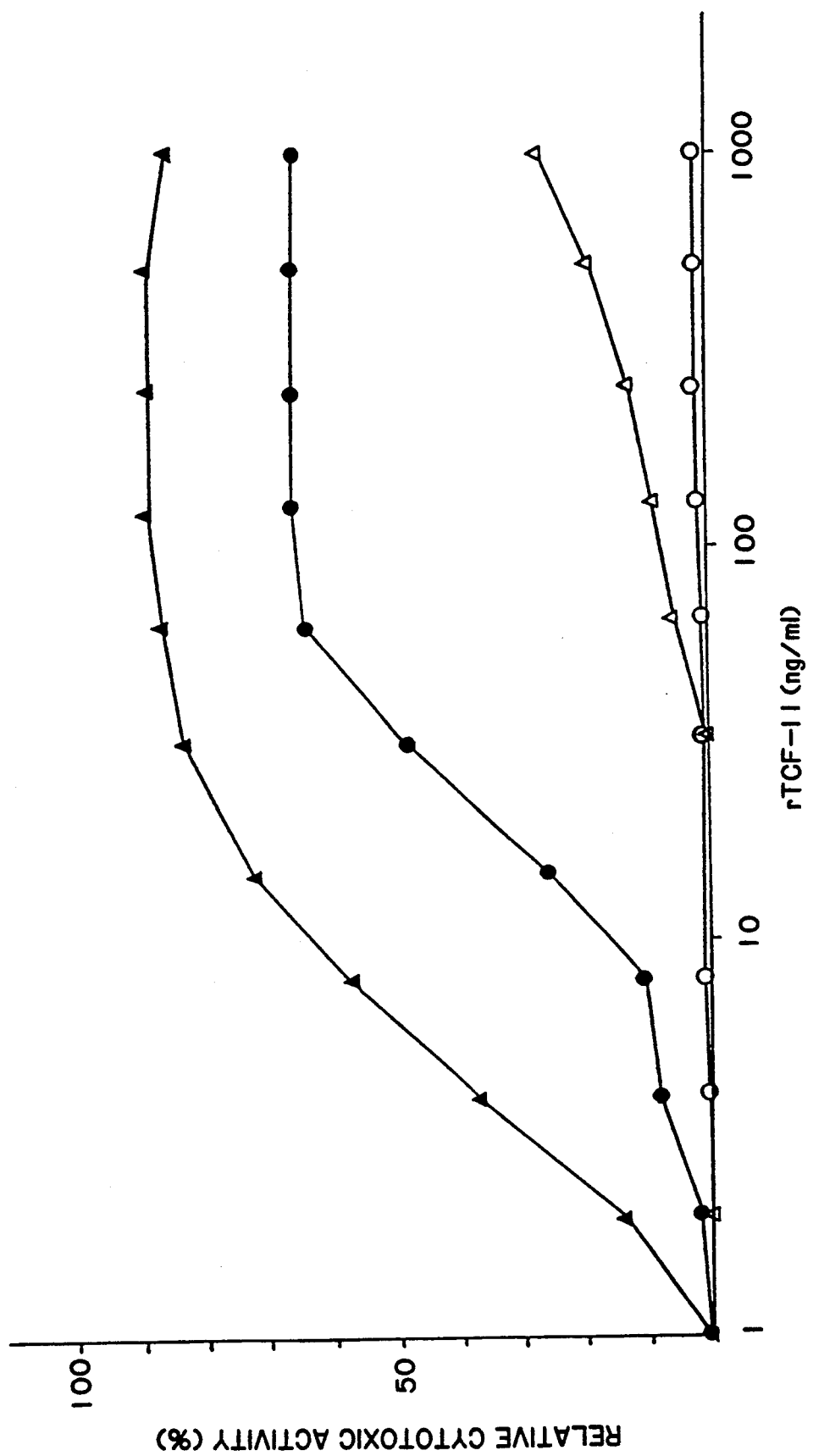
FIG. 10 shows cytotoxic activities of rTCF-II against various tumor cell lines. In the figure, — ▲ — , — ● — , and — — show the cytotoxic activities of rTCF-II against Sarcoma 180, Meth A sarcoma, KB and IMR-90 cells, respectively.

Cytotoxic activity of rTCF-II against the tested cell lines was shown in FIG. 10.

rTCF-II had a potent cytotoxic activity against Sarcoma 180 and Meth A sarcoma, and also cytotoxic activity against KB. rTCF-II, however, did not have any cytotoxic activity against normal cells, IMR-90.

2) Hepatocyte growth stimulating activity

Figure 11:
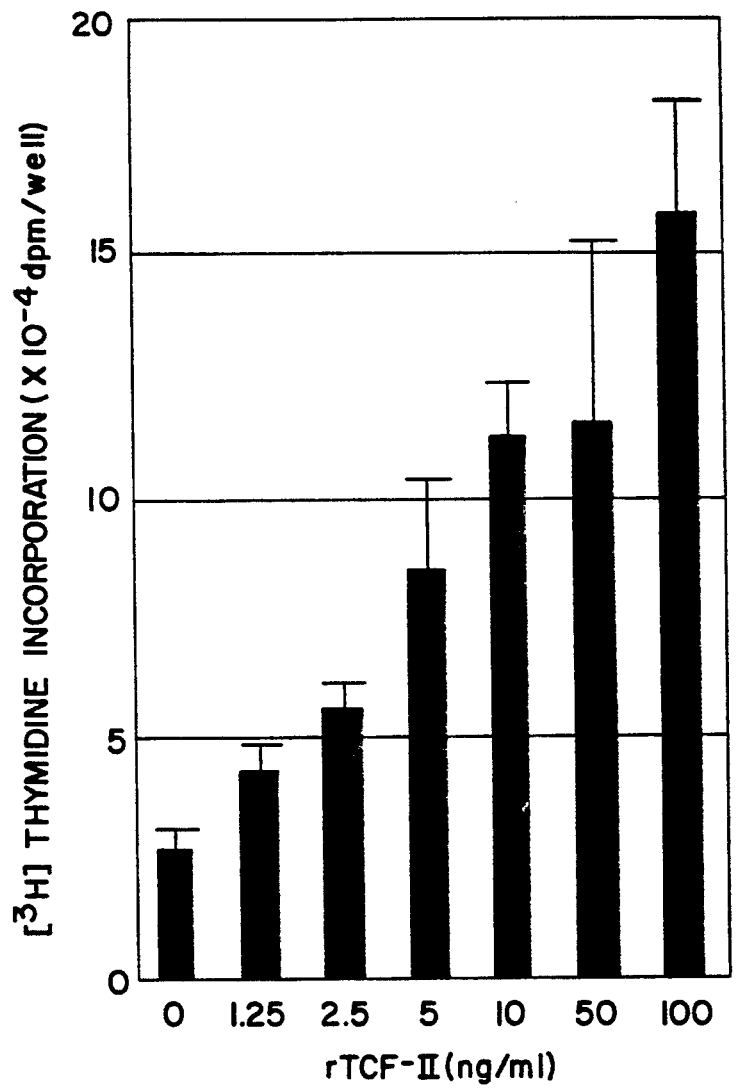
FIG. 11 shows hepatocyte growth stimulating activity of rTCF-II.

Hepatocytes were separated from Wister male rat, 200 g by the method of Segren (Method in Cell Biology, Vol. 13, P29, Academic Press, New York, 1976). The obtained hepatocytes were seeded into each well in 24-well plates (Falcon) at a cell density of $8.8 \times 10^4$ cells/0.5 ml/well and cultured at 37° C. . William E culture medium (Flow Laboratory) supplemented with 10% fetal calf serum (FCS) and 10μM dexamethasone was used as a culture medium (abbreviated below as basal culture medium). After incubation at 37° C. for 24 hours, the culture broth was exchanged with the basal culture medium containing rTCF-II. The hepatocytes were further cultured for 24 hours and then cultured in the basal culture medium containing 4 μCi/ml of $^3$H-thymidine (Amersham) for 2 hours. After cultivation, the cells were washed twice with cold PBS, 5% perchloric acid and 95% ethanol, respectively and air-dried. The cells were solubilized in 10% SDS solution containing 10 mM $MgCl_2$ and DNA synthesis of the cells was determined by measuring radioactivities, using a liquid scintillation counter. Hepatocyte growth stimulating activity of rTCF-II was shown in FIG. 11.

Industrial Applicability

The present invention provides a large scale and economical production of TCF-II, which is carried out by construction of TCF-II expression vector containing DNA encoding the amino acid sequence of TCF-II and by production of rTCF-II by recombinant technology using the expression vector. rTCF-II obtained in the present invention can be used in the field of pharmaceutical products as a hepatocyte growth factor, a tumor cytotoxic factor, etc. Moreover, rTCF-II in the present invention can be used as a biochemical or a pharmacological reagent.

Commentaries on Transformants 1. pcTCF(s)/MC1061/P3

Deposit Agency

Name: Fermentation Research Institute; Agency of Industrial Science and Technology, Ministry of International Trade and Industry Addresss: 1-3 Higashi-1 choume, Tsukuba-shi, Ibaragi-ken, Japan Deposit date: Jul. 13 1990.

Deposit number: FERM BP- 3479 [Deposit based on Butapest treaty: Transferred from a deposit in Japan (deposit number, FERM P - 11605)]

2. TCdG₂H₃C₂

Deposit Agency

Name: Fermentation Research Institute; Agency of Industrial Science and Technology, Ministry of International Trade and Industry Address: 1-3 Higashi-1 choume, Tsukuba-shi, Ibaragi-ken, Japan
Deposit date: Jul. 10 1991
Deposit number: FERM BP-3480

---

I claim:

1. A plasmid comprising a DNA encoding the amino acid sequence of TCF-II, wherein said DNA has a sequence shown in FIG. 1 (SEQ ID NO:2).

2. A mammalian host cell transformed with the plasmid according to claim 1.

3. A host cell according to claim 2, which is deposited at the Fermentation Research Institute; Agency of Industrial Science and Technology under deposit number, FERM BP-3479.

4. A host cell according to claim 2, which is deposited at the Fermentation Research Institute; Agency of Industrial Science and Technology under deposit number, FERM BP-3480.

5. A method for the production of rTCF-II which comprises culturing mammalian host cells transformed with the plasmids of claim 1 under conditions wherein said cells express rTCF-II encoded by said plasmids, and purifying the resulting rTCF-II from the culture broth.

* * * * *